(12) United States Patent
Morishita et al.

(10) Patent No.: US 7,795,258 B2
(45) Date of Patent: Sep. 14, 2010

(54) PYRIDAZINE COMPOUND AND USE THEREOF

(75) Inventors: Hiroshi Morishita, Oita (JP); Akio Manabe, Sanda (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 521 days.

(21) Appl. No.: 11/630,345

(22) PCT Filed: Jun. 2, 2005

(86) PCT No.: PCT/JP2005/010541

§ 371 (c)(1),
(2), (4) Date: Dec. 21, 2006

(87) PCT Pub. No.: WO2006/001175

PCT Pub. Date: Jan. 5, 2006

(65) Prior Publication Data

US 2008/0275050 A1    Nov. 6, 2008

(30) Foreign Application Priority Data

Jun. 28, 2004  (JP) .............................. 2004-189396

(51) Int. Cl.
*C07D 237/08* (2006.01)
*A61K 31/50* (2006.01)
*A61P 31/10* (2006.01)
*C07C 205/06* (2006.01)
*C07C 49/303* (2006.01)

(52) U.S. Cl. ...................... 514/247; 544/224; 568/308; 568/306; 568/325

(58) Field of Classification Search ................. 514/247; 544/224

See application file for complete search history.

(56) References Cited

U.S. PATENT DOCUMENTS 5,077,142 A * 12/1991 Sakon et al. ................. 428/690

FOREIGN PATENT DOCUMENTS

| EP | 1 767 529 A1 | 3/2007 |
|---|---|---|
| JP | 55-111472 | 8/1980 |
| JP | 56-113767 | 9/1981 |
| WO | WO 99/10331 | 3/1999 |

OTHER PUBLICATIONS

Myclobutanil, <http://www.chinayifan.com/pages/myclobutanil-e.htm>, 2006, downloaded Feb. 14, 2009.*
Gonella, et al., Bull. Insectology, 61(1):221-222, 2008.*

Berry, R.W.H. et al., "4,5-Diphenylpyridazine: Preparation and Ultraviolet Spectrum", J. Chem. Soc., 1970, vol. 9, p. 1316.
Chambers, Richard D. et al., "Polyfluroheterocyclic Compounds. Part XXIV. Thermal Elimination of Molecular Nitrogen from Polyfluro- and Polychloro-pyridazines", J. Chem. Soc. Perkin Transactions I, 1974, (I), pp. 125-129.
Felluga, F. et al., "Carbo- and Heterocyclization Reactions of 2-(4-Morpholinyl)-1-Phenylpropene and Nitroolefins", Tetrahedron, 1989, vol. 45, No. 17, pp. 5667-5678.
Klyuev, N. A. et al., "Chromatographic-mass Sepctrometric Study of Azines of Alkyl Benzyl Ketones and Products of Their Thermal Transformation", Zhurnal Organicheskoi Khimii, 1979, vol. 15, No. 11, pp. 2274-2280.
Krapf, H. et al., "Thermische Umwandlung der labilen 1: 1-Addukte aus Diphenylcyclopropenon bzw. Diphenylcyclopropenthion und Ketenacetalen", 1976, vol. 109, No. 2, pp. 576-596.
Lai, Yee-Hing et al., "Synthesis and Diatropicity of trans-2',5',10lb,10c-tetramethylfurano[3,4-e]-10b,10c-dihydropyrene. A Valence Isomerization to Form a Novel Isoannulenofuran at the Expense of Two Benzene and One Furan Rings", J. Org. Chem, 1996, vol. 61, pp. 935-940.
Lai, Yee-Hing et al., "Synthesis and Diatropicity of trans-N-Cyclohexyl-2',5',10lb,10c-tetramethylpyrrolo[3,4-e]-10b,10c-dihydropyrene. The First Example of an Iso[17]annulenopyrrole", J. Org. Chem, 1997, vol. 62, No. 17, pp. 6060-6063.
Pattabiraman, Vijaya et al., "Synthesis of 3,4-Diarylsubstituted Maleic Anhydride/Maleimide via Unusual Oxidative Cyclization of Phenacyl Ester/Amide", Synlett, 2002, No. 6, pp. 947-951.

* cited by examiner

*Primary Examiner*—James O Wilson
*Assistant Examiner*—Cecilia M Jaisle
(74) *Attorney, Agent, or Firm*—Foley & Lardner LLP

(57) ABSTRACT

A pyridazine compound represented by formula (1):

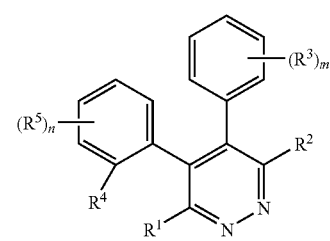

(1)

wherein $R^1$ and $R^2$ are same or different and represent a C1-C4 alkyl group; $R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom; $R^4$ and $R^5$ each represents a halogen atom, a nitro group, a cyano group, a C1-C4 alkyl group optionally substituted by at least one halogen atom or a C1-C4 alkoxy group optionally substituted by at least one halogen atom; and m and n each represents an integer.

5 Claims, No Drawings

PYRIDAZINE COMPOUND AND USE THEREOF

TECHNICAL FIELD

The present invention relates to a pyridazine compound, use thereof and its production intermediate.

BACKGROUND ART

Conventionally, agricultural fungicides have been developed, and a lot of compounds having a fungicidal activity have been found. However, a plant disease controlling effect of these compound's is not necessarily sufficient, and novel compounds having a plant disease controlling effect are searched.

DISCLOSURE OF THE INVENTION

The present inventors have intensively studied to find a compound having an excellent plant disease controlling effect, and resultantly found that a pyridazine compound represented by the following formula (1) has an excellent plant disease controlling activity, completing the present invention.

That is, the present invention is as described in the following items 1 to 6.

1. A pyridazine compound represented by formula (1) (referred to as the compound of the present invention, hereinafter):

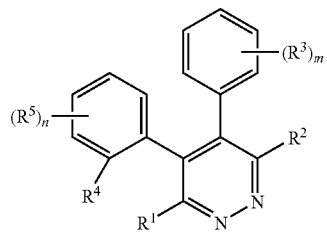

wherein, $R^1$ and $R^2$ are same or different and represent a C1-C4 alkyl group;

$R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;

m represents an integer of 0 to 5; provided that, when m represents an integer of 2 or more, each of $R^3$s is same or different;

$R^4$ represents a halogen atom, a nitro group, a cyano group, a C1-C4 alkyl group optionally substituted by at least one halogen atom or a C1-C4 alkoxy group optionally substituted by at least one halogen atom;

$R^5$ represents a halogen atom, a nitro group, a cyano group, a C1-C4 alkyl group optionally substituted by at least one halogen atom or a C1-C4 alkoxy group optionally substituted by at least one halogen atom;

n represents an integer of 0 to 4; provided that, when n represents an integer of 2 or more, each of $R^5$s is same or different.

2. A fungicidal composition comprising the compound of the present invention as an active ingredient.

3. A method for controlling plant diseases comprising applying an effective amount of the compound of the present invention to plants or soils growing the plants.

4. Use of the compound of the present invention as an active ingredient of a fungicidal composition.

5. A compound represented by formula (3):

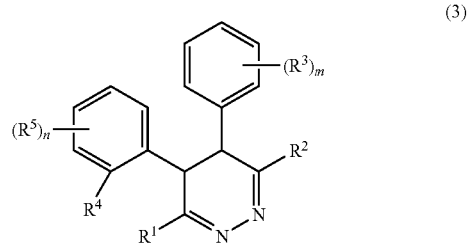

wherein, $R^1$ and $R^2$ are same or different and represent a C1-C4 alkyl group;

$R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;

m represents an integer of 0 to 5; provided that, when m represents an integer of 2 or more, each of $R^3$s is same or different;

$R^4$ represents a halogen atom, a nitro group, a cyano group, a C1-C4 alkyl group optionally substituted by at least one halogen atom or a C1-C4 alkoxy group optionally substituted by at least one halogen atom;

$R^5$ represents a halogen atom, a nitro group, a cyano group, a C1-C4 alkyl group optionally substituted by at least one halogen atom or a C1-C4 alkoxy group optionally substituted by at least one halogen atom;

n represents an integer of 0 to 4; provided that, when n represents an integer of 2 or more, each of $R^5$s is same or different.

6. A compound represented by formula (2-1):

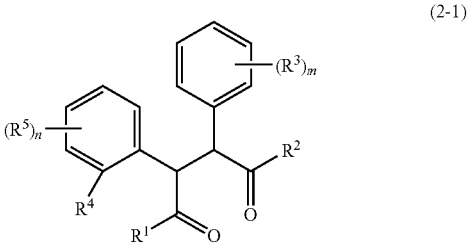

wherein, $R^1$ and $R^2$ are same or different and represent a C1-C4 alkyl group;

$R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;

m represents an integer of 0 to 5; provided that, when m represents an integer of 2 or more, each of $R^3$s is same or different;

$R^{41}$ represents a halogen atom;

$R^5$ represents a halogen atom, a nitro group, a cyano group, a C1-C4 alkyl group optionally substituted by at least one halogen atom or a C1-C4 alkoxy group optionally substituted by at least one halogen atom;

n represents an integer of 0 to 4; provided that, when n represents an integer of 2 or more, each of $R^5$s is same or different.

Next, substituents on the compounds of the present invention and the like will be described.

In the formula (1), the C1-C4 alkyl group represented by $R^1$ or $R^2$ includes, for example, a methyl group and an ethyl group.

The C1-C4 alkyl group optionally substituted by at least one halogen atom represented by $R^3$ includes, for example, a methyl group, and an ethyl group, an isopropyl group, a tert-butyl group, a trifluoromethyl group, a difluoromethyl group and a fluoromethyl group;

the C1-C4 alkoxy group optionally substituted by at least one halogen atom includes, for example, a methoxy group, an ethoxy group, an isopropoxy group, a trifluoromethoxy group, a difluoromethoxy group, a fluoromethoxy group, a chlorodifluoromethoxy group, a bromodifluoromethoxy group, a 1,1,2,2-tetrafluoroethoxy group and a 2,2,2-trifluoroethoxy group;

the C1-C4 alkylthio group optionally substituted by at least one halogen atom includes, for example, a methylthio group, an ethylthio group, a trifluoromethylthio group, and a 1,1,2,2-tetrafluoroethylthio group.

The halogen atom represented by $R^3$, $R^4$ and $R^5$ includes a fluorine atom, a chlorine atom, a bromine atom and an iodine atom.

The C1-C4 alkyl group optionally substituted by at least one halogen atom represented by $R^4$ or $R^5$ includes, for example, a methyl group, an ethyl group, a trifluoromethyl group, a difluoromethyl group and a fluoromethyl group;

the C1-C4 alkoxy group optionally substituted by at least one halogen atom includes, for example, a methoxy group, an ethoxy group, a trifluoromethoxy group, a difluoromethoxy group and a fluoromethoxy group.

In the formula (1), the phenyl group substituted by $R^4$ and $(R^5)_n$ includes, for example, groups in which n is 0, that is, a 2-chlorophenyl group, a 2-nitrophenyl group, a 2-cyanophenyl group, a 2-methylphenyl group, a 2-(trifluoromethyl)phenyl group, a 2-methoxyphenyl group, a 2-(difluoromethoxy)phenyl group, a 2-(trifluoromethoxy)phenyl group; groups in which n is 1, that is, a 2,3-difluorophenyl group, a 2,3-dichlorophenyl group, a 2,4-difluorophenyl group, a 2-chloro-4-fluorophenyl group, a 4-chloro-2-fluorophenyl group, a 2,4-dichlorophenyl group, a 2,5-difluorophenyl group, a 2,6-difluorophenyl group, a 2-chloro-6-fluorophenyl group, a 2,6-dichlorophenyl group, a 2-fluoro-6-methylphenyl group, a 2-fluoro-6-nitrophenyl group, a 2-cyano-6-fluorophenyl group, a 2-fluoro-6-(trifluoromethyl)phenyl group, a 2-(difluoromethoxy)-6-fluorophenyl group, a 2-fluoro-6-(trifluoromethoxy)phenyl group, a 2-fluoro-6-methoxyphenyl group; groups in which n is 2, that is, a 2,3,4-trifluorophenyl group, a 2,3,5-trifluorophenyl group, 2,4,5-trifluorophenyl group, a 2,3,6-trifluorophenyl group, a 2,4,6-trifluorophenyl group, a 2-chloro-4,6-difluorophenyl group, a 4-chloro-2,6-difluorophenyl group, a 2,6-difluoro-4-ethoxyphenyl group, a 2,6-difluoro-4-methoxyphenyl group, a 2,4-dichloro-6-fluorophenyl group, a 2,6-dichloro-4-fluorophenyl group, a 2,4,6-trichlorophenyl group, a 2,6-difluoro-4-cyanophenyl group, a 2,6-difluoro-4-nitrophenyl group, a 2,6-difluoro-4-(trifluoromethyl)phenyl group, a 2,3-difluoro-6-(trifluoromethyl)phenyl group, a 2,6-difluoro-3-chlorophenyl group; groups in which n is 3, that is, a 2,3,4,5-tetrafluorophenyl group, a 2,3,4,6-tetrafluorophenyl group, a 2,3,5,6-tetrafluorophenyl group; and groups in which n is 4, that is, a 2,3,4,5,6-pentafluorophenyl group, a 4-methoxy-2,3,5,6-tetrafluorophenyl group, a 4-ethoxy-2,3,5,6-tetrafluorophenyl group, a 4-cyano-2,3,5,6-tetrafluorophenyl group, a 4-nitro-2,3,5,6-tetrafluorophenyl group and a 4-chloro-2,3,5,6-tetrafluorophenyl group.

The phenyl group substituted by $(R^3)_m$ includes, for example, a phenyl group; groups in which m is 1, that is, a 4-methylphenyl group, a 3-methylphenyl group, a 2-methylphenyl group, a 4-ethylphenyl group, a 4-isopropylphenyl group, a 4-tert-butylphenyl group, a 4-(trifluoromethyl)phenyl group, a 3-(trifluoromethyl)phenyl group, a 4-chlorophenyl group, a 3-chlorophenyl group, a 2-chlorophenyl group, a 4-fluorophenyl group, a 3-fluorophenyl group, a 2-fluorophenyl group, a 4-methoxyphenyl group, a 3-methoxyphenyl group, a 4-ethoxyphenyl group, a 4-(trifluoromethoxy)phenyl group, a 4-nitrophenyl group, a 4-cyanophenyl group, a 4-(methylthio)phenyl group, a 4-(trifluoromethythio)phenyl group; and groups in which m is 2, that is, a 2,4-dimethylphenyl group, a 2,5-dimethylphenyl group, a 3,4-dimethylphenyl group, a 2,4-dichlorophenyl group, a 2,5-dichlorophenyl group, a 3,4-dichlorophenyl group, a 2,3-difluorophenyl group, a 2,4-difluorophenyl group, a 2,5-difluorophenyl group, a 3,4-difluorophenyl group, a 3,5-difluorophenyl group, a 4-chloro-2-fluorophenyl group, a 2,4-dimethoxyphenyl group and a 3,4-dimethoxyphenyl group.

Embodiments of the compound of the present invention include, for example, the following compounds.

Pyridazine compounds of the formula (1) in which $R^1$ is a methyl group;

pyridazine compounds of the formula (1) in which $R^2$ is a methyl group;

pyridazine compounds of the formula (1) in which $R^1$ and $R^2$ are methyl groups;

pyridazine compounds of the formula (1) in which $R^3$ is a C1-C4 alkyl group optionally substituted by at least one halogen atom, a C1-C4 alkoxy group optionally substituted by at least one halogen atom, or a halogen atom;

pyridazine compounds of the formula (1) in which $R^3$ is a C1-C4 alkyl group or a halogen atom;

pyridazine compounds of the formula (1) in which $R^3$ is a methyl group, a trifluoromethyl group, a chlorine atom, a fluorine atom or a methoxy group;

pyridazine compounds of the formula (1) in which $R^3$ is a methyl group, a chlorine atom or a fluorine atom;

pyridazine compounds of the formula (1) in which m is 1 or 2;

pyridazine compounds of the formula (1) in which m is 1;

pyridazine compounds of the formula (1) in which m is 2;

pyridazine compounds of the formula (1) in which m is 1, and $R^3$ is a substituent in the 4 position of benzene ring;

pyridazine compounds of the formula (1) in which m is 1, $R^3$ is a halogen atom, a C1-C4 alkyl group optionally substituted by at least one halogen atom, or at least one C1-C4 alkoxy group optionally substituted by at least one halogen atom, and $R^3$ is a substituent in the 4 position of benzene ring;

pyridazine compounds of the formula (1) in which m is 1, $R^3$ is a halogen atom or a C1-C4 alkyl group optionally substituted by at least one halogen atom, and $R^3$ is a substituent in the 4 position of benzene ring;

pyridazine compounds of the formula (1) in which m is 1, $R^3$ is a halogen atom or a C1-C4 alkyl group, and $R^3$ is a substituent in the 4 position of benzene ring;

pyridazine compounds of the formula (1) in which m is 1, $R^3$ is a methyl group, a trifluoromethyl group, a chlorine atom, a fluorine atom, or a methoxy group, and $R^3$ is a substituent in the 4 position of benzene ring;

pyridazine compounds of the formula (1) in which m is 1, $R^3$ is a methyl group, a chlorine atom, or a fluorine atom, and $R^3$ is a substituent in the 4 position of benzene ring;

pyridazine compounds of the formula (1) in which $R^4$ is a halogen atom;

pyridazine compounds of the formula (1) in which $R^4$ is a fluorine atom;

pyridazine compounds of the formula (1) in which $R^4$ is a chlorine atom;

pyridazine compounds of the formula (1) in which $R^4$ is a fluorine atom or a chlorine atom;

pyridazine compounds of the formula (1) in which n is 1 or 2;

pyridazine compounds of the formula (1) in which n is 1;

pyridazine compounds of the formula (1) in which n is 2;

pyridazine compounds of the formula (1) in which n is 1 or 2, and $R^5$ is a halogen atom;

pyridazine compounds of the formula (1) in which n is 1, $R^5$ is a halogen atom, and $R^5$ is a substituent in the 4 position or the 6 position of benzene ring;

pyridazine compounds of the formula (1) in which n is 2, $R^5$ is a halogen atom, and
$R^5$s are substituents in the 4 position and 6 position of benzene ring;

pyridazine compounds of the formula (1) in which n is 1, $R^5$ is a fluorine atom, and
$R^5$ is a substituent in the 4 position or 6 position of benzene ring;

pyridazine compounds of the formula (1) in which n is 2, $R^5$ is a fluorine atom, and
$R^5$s are substituents in the 4 position and 6 position of benzene ring;

pyridazine compounds of the formula (1) in which $R^4$ is a halogen atom, n is 1 or 2, and each $R^5$ is a halogen atom;

pyridazine compounds of the formula (1) in which n is 1, $R^4$ is a halogen atom, $R^5$ is a halogen atom, and $R^5$ is a substituent in the 4 position or 6 position of benzene ring;

pyridazine compounds of the formula (1) in which n is 2, $R^4$ is a halogen atom, $R^5$ is a halogen atom, and $R^5$s are substituents in the 4 position and 6 position of benzene ring;

pyridazine compounds of the formula (1) in which n is 1, $R^4$ is a fluorine atom, $R^5$ is a fluorine atom, and $R^5$ is a substituent in the 4 position or 6 position of benzene ring;

pyridazine compounds of the formula (1) in which n is 2, $R^4$ is a fluorine atom, $R^5$ is a fluorine atom, and $R^5$ is a substituent in the 4 position or 6 position of benzene ring;

pyridazine compounds of the formula (1) in which n is 0;

pyridazine compounds of the formula (1) in which n is 0, 1 or 2, m is 1 or 2;

pyridazine compounds of the formula (1) in which each of $R^1$ and $R^3$ is a methyl group, and $R^4$ is a halogen atom; and pyridazine compounds of the formula (1) in which n is 0, 1 or 2, m is 1 or 2, each of $R^1$ and $R^3$ is a methyl group, and $R^4$ is a halogen atom.

Embodiments of the compound represented by the formula (2-1) and the compound represented by the formula (3), which are intermediate compound of the present invention, include, for example, the following compounds.

Compounds of the formula (2-1) in which n is 0, 1 or 2, and m is 1 or 2;

compounds of the formula (2-1) in which each of $R^1$ and $R^2$ is a methyl group;

compounds of the formula (2-1) in which n is 0, 1 or 2, m is 1 or 2, and each of $R^1$ and $R^2$ is a methyl group;

compounds of the formula (3) in which n is 0, 1 or 2, and m is 1 or 2;

compounds of the formula (3) in which each of $R^1$ and $R^2$ is a methyl group, and $R^4$ is a halogen atom; and compounds of the formula (3) in which n is 0, 1 or 2, m is 1 or 2, each of $R^1$ and $R^2$ is a methyl group, and $R^4$ is a halogen atom.

Next, the method of producing the compound of the present invention will be described.

The compound of the present invention can be produced, for example, by the following (Production method 1), (Production method 2) and (Production method 3).

(Production Method 1)

The compound of the present invention can be produced from the compound represented by the formula (2) in the following route.

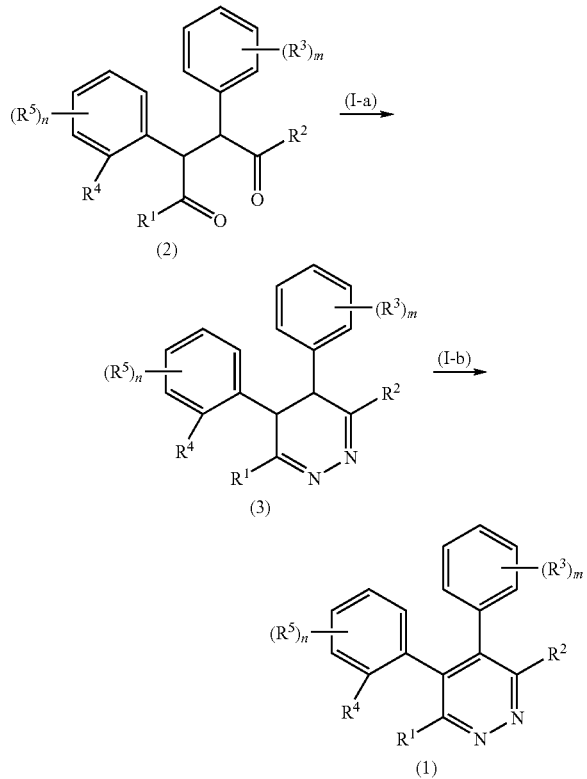

(wherein, $R^1$ and $R^2$ are the same or different and each is a C1-C4 alkyl group;

$R^3$ is a halogen atom, a nitro group, a cyano group, a C1-C4 alkyl group optionally substituted by at least one halogen atom, a C1-C4 alkoxy group optionally substituted by at least one halogen atom, or a C1-C4 alkylthio group optionally substituted by at least one halogen atom;

m is an integer of 0 to 5; provided that, when m is an integer of 2 or more, each of $R^3$s is the same or different;

$R^4$ is a halogen atom, a nitro group, a cyano group, a C1-C4 alkyl group optionally substituted by at least one halogen atom, or a C1-C4 alkoxy group optionally substituted by at least one halogen atom;

$R^5$ is a halogen atom, a nitro group, a cyano group, a C1-C4 alkyl group optionally substituted by at least one halogen atom, or a C1-C4 alkoxy group optionally substituted by at least one halogen atom; and n is an integer of 0 to 4; provided that, when n is an integer of 2 or more, each of $R^5$s is the same or different.)

Step (I-a) will be described.

The compound represented by the formula (3) can be produced by reacting the compound represented by the formula (2) with a hydrazine.

The reaction is usually carried out in a solvent.

Examples of the solvent used in the reaction include alcohols such as methanol, ethanol, propanol and isopropanol; ethers such as tetrahydrofuran and 1,2-dimethoxyethane; and mixtures thereof.

The amount of the hydrazine used in the reaction is usually a proportion of 1 to 5 per 1 mole of the compound represented by the formula (2). Hydrazine used in the reaction may be its hydrate.

The reaction temperature is usually in a range of 0 to 80° C., and the reaction time is usually in a range of 1 to 24 hours.

After completion of the reaction, the reaction mixture can be subjected to a post treatment operation such as concentration to isolate the compound represented by the formula (3). Also the reaction mixture may be used in the reaction of the next Step (I-b) as it is.

Next, Step (I-b) will be described.

The compound of the present invention can be produced by reacting the compound represented by the formula (3) with an oxidizing agent.

The reaction is usually carried out in a solvent.

The oxidizing agent used in the reaction includes, for example, platinum oxide ($PtO_2$), lead dioxide ($PbO_2$) and the like.

Examples of the solvent used in the reaction include alcohols such as methanol, ethanol, propanol and isopropanol, ethers such as tetrahydrofuran and 1,2-dimethoxyethane, water, and mixtures thereof.

The amount of the oxidizing agent used in the reaction is usually a proportion of 1 to 5 mol per 1 mol of the compound represented by the formula (3).

The reaction temperature is usually in a range of 40 to 80° C., and the reaction time is usually in a range of 1 to 48 hours.

After completion of the reaction, the reaction mixture is subjected to a post treatment operation, for example, in which the reaction mixture is filtered, and the filtrate is concentrated; thus the present compound can be isolated. The compound isolated can also be further purified by chromatography, re-crystallization and the like.

(Production Method 2)

The compound of the present invention can be produced by reacting the compound represented by the formula (4) with a base.

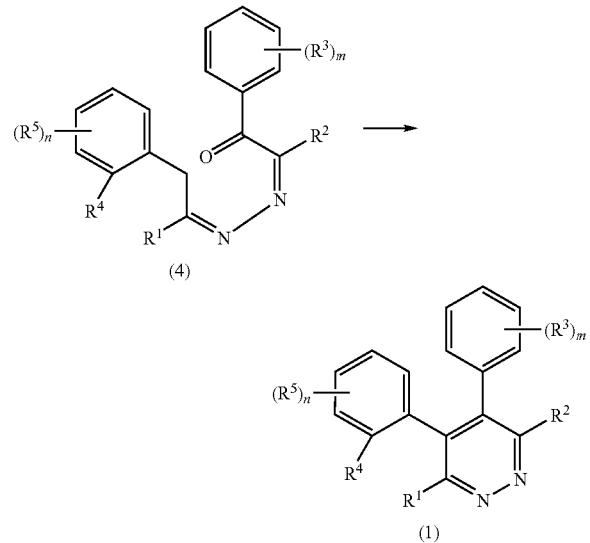

(wherein $R^1$, $R^2$, $R^3$, m, $R^4$, $R^5$ and n are the same meanings as defined above.

The reaction is usually carried out in a solvent.

Examples of the solvent used in the reaction include alcohols such as methanol, ethanol, propanol, isopropanol and tert-butanol, ethers such as tetrahydrofuran and 1,2-dimethoxyethane, and mixtures thereof.

The base used in the reaction includes, for example, alkali metal hydroxides such as potassium hydroxide and sodium hydroxide.

The amount of the base used in the reaction is usually 1 to 2 mole per 1 mol of the compound represented by the formula (4).

The reaction temperature is usually in a range of 0 to 100° C., and the reaction time is usually in a range of 0.1 to 8 hours.

After completion of the reaction, the reaction mixture is subjected to a post treatment operation, for example, in which the reaction mixture is mixed with water, the mixture is extracted with an organic solvent, and the resulting organic layer is dried and concentrated, and the like; thus, the present compound can be isolated. The present compound isolated can also be further purified by chromatography, re-crystallization and the like.

Next, the method for producing intermediate compounds of the present compound will be shown as Reference Production method.

(Reference Production Method 1)

The compound represented by the formula (2) can be produced, for example, from the compound represented by the formula (6) and the compound represented by the formula (7), according to the following scheme.

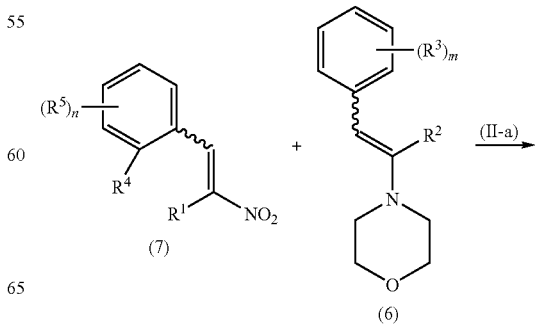

-continued

[structure (5) with substituents $(R^5)_n$, $(R^3)_m$, $R^1$, $R^2$, $R^4$, and N⁺–OH / O⁻ group] (II-b)→

[structure (2) with substituents $(R^5)_n$, $(R^3)_m$, $R^1$, $R^2$, $R^4$, and C=O groups]

(wherein $R^1$, $R^2$, $R^3$, m, $R^4$, $R^5$ and n are the same meaning as defined above.)

Step (II-a)

The reaction is carried out in the absence or presence of a solvent.

Examples of the solvent used in the reaction include hydrocarbons such as toluene and xylene.

The amount of the compound represented by the formula (7) is usually a proportion of 0.8 to 1.3 mol per 1 mole of the compound represented by the formula (6).

The reaction temperature is usually in a range of 0 to 50° C., and the reaction time is usually in a range of 1 to 48 hours.

After completion of the reaction, the reaction mixture is concentrated, and usually the residue is used in the reaction of Step (II-b).

Step (II-b)

The reaction is carried out by mixing the reaction product in Step (II-a) with an acid.

The reaction is usually carried out in the presence of water and an organic solvent.

Examples of the organic solvent used in the reaction include, for example, alcohols such as methanol and ethanol, ethers such as tetrahydrofuran and 1,4-dioxane, and mixtures thereof.

The reaction is usually carried out at pH of around 2. The acid used in the reaction includes, for example, hydrochloric acid.

The reaction temperature is usually in a range of 0 to 30° C., and the reaction time is usually in a range of 1 to 48 hours.

After completion of the reaction, the reaction mixture can be concentrated to isolate the compound represented by the formula (2). The compound represented by the formula (2) isolated can also be further purified by re-crystallization, chromatography and the like.

The compound represented by the formula (6) can be produced in the same manner as that described in, for example, J. Org. Chem., 32, pp. 213-214 (1967).

The compound represented by the formula (7) can be produced in the same manner as that described in, for example, J. Med. Chem., 29, pp. 924-939 (1986).

(Reference Production Method 2)

The compound represented by the formula (4) can be produced by reacting the compound represented by the formula (8) with the compound represented by the formula (9) in the presence of an acid.

[structure (9) with $(R^5)_n$, $R^4$, $R^1$, C=O] + [structure (8) with $(R^3)_m$, $R^2$, C=O, C=N–NH₂] →

[structure (4) with $(R^5)_n$, $(R^3)_m$, $R^1$, $R^2$, $R^4$, C=O and C=N–N groups]

(wherein $R^1$, $R^2$, $R^3$, m, $R^4$, $R^5$ and n are the same meanings as defined above.)

The reaction is usually carried out in the presence of a solvent.

Examples of the solvent used in the reaction include hydrocarbons such as toluene and xylene.

The acid used in the reaction includes, for example, organic sulfonic acids such as p-toluene sulfonic acid.

As to the amounts of the reagents used in the reaction, usually, the compound represented by the formula (9) is used in a proportion of 0.8 to 1.3 mol per 1 mol of the compound represented by the formula (8), and the acid is used in a proportion of 0.001 to 0.05 mol per 1 mol of the compound represented by the formula (8).

The reaction temperature is usually in a range of 20 to 120° C., and the reaction time is usually in a range of 1 to 8 hours.

The reaction is usually carried out while dehydrating with Dean-Stark trap.

After completion of the reaction, the reaction mixture is subjected to a post treatment operation, for example, in which (1) the reaction mixture is concentrated, (2) the reaction mixture is mixed with an aqueous sodium hydrogen carbonate solution, the mixture is extracted with an organic solvent, and the resulting organic layer is dried and concentrated, and the like; thus, the compound represented by the formula (4) can be isolated.

The compound represented by the formula (4) isolated can also be further purified by chromatography, re-crystallization and the like.

(Reference Production Method 3)

The compound represented by the formula (8) can be produced by reacting the compound represented by the formula (10) with a hydrazine.

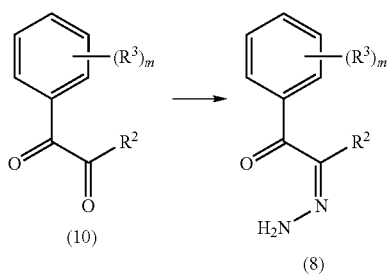

(wherein $R^2$, $R^3$ and m are the same meaning as defined above.)

The reaction is carried out in the presence of a solvent.

Examples of the solvent used in the reaction include alcohols such as ethanol.

The amount of the hydrazine used in the reaction is usually a proportion of 0.8 to 1.3 mole per 1 mole of the formula (10).

Hydrazine used in the reaction may be its hydrate.

The reaction temperature is usually in a range of 0 to 80° C., and the reaction time is usually in a range of 1 to 48 hours.

After completion of the reaction the reaction mixture is subjected to a post treatment such as concentration, thus the compound represented by the formula (8) can be isolated. The compound represented by the formula (8) isolated can also be further purified by chromatography, re-crystallization and the like.

As the compound represented by the formula (10) may be used commercially available compounds; or compounds produced in the same manner as in, for example, J. Org. Chem., 43, pp. 2933-2935 (1978) or Synthesis, pp. 403-404, (1977) may be used. As the compound represented by the formula (9) may be commercially available compounds, or compound produced in the same manner as in, for example, J. Med. Chem., 29, pp. 924-939 (1986) may be used.

Next, specific examples of the compound of the present invention will be shown.

Pyridazine compound represented by the formula (1-a):

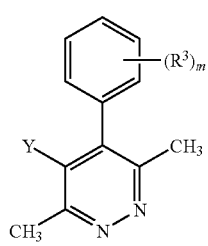

In the formula (1-a), $(R^3)_m$ and Y represent one combination of substituents shown in Table 1.

TABLE 1

| $(R^3)_m$ | Y |
|---|---|
| 4-CH$_3$ | 2-(trifluoromethyl)phenyl |
| 4-Cl | 2-(trifluoromethyl)phenyl |
| 4-CH$_3$ | 2-(difluoromethoxy)phenyl |
| 4-Cl | 2-(difluoromethoxy)phenyl |
| 4-CH$_3$ | 2,4,6-trifluorophenyl |
| 3-CH$_3$ | 2,4,6-trifluorophenyl |
| 2-CH$_3$ | 2,4,6-trifluorophenyl |

TABLE 1-continued

| $(R^3)_m$ | Y |
|---|---|
| 4-CF$_3$ | 2,4,6-trifluorophenyl |
| 4-Cl | 2,4,6-trifluorophenyl |
| 3-Cl | 2,4,6-trifluorophenyl |
| 2-Cl | 2,4,6-trifluorophenyl |
| 4-F | 2,4,6-trifluorophenyl |
| 4-NO$_2$ | 2,4,6-trifluorophenyl |
| 4-CN | 2,4,6-trifluorophenyl |
| 4-OCH$_3$ | 2,4,6-trifluorophenyl |
| 4-OCF$_3$ | 2,4,6-trifluorophenyl |
| 4-OCHF$_2$ | 2,4,6-trifluorophenyl |
| 4-OCClF$_2$ | 2,4,6-trifluorophenyl |
| 4-OCBrF$_2$ | 2,4,6-trifluorophenyl |
| 4-SCH$_3$ | 2,4,6-trifluorophenyl |
| 4-SCF$_3$ | 2,4,6-trifluorophenyl |
| — | 2,4,6-trifluorophenyl |
| 2-Cl,4-Cl | 2,4,6-trifluorophenyl |
| 3-Cl,4-Cl | 2,4,6-trifluorophenyl |
| 2-CH$_3$,4-CH$_3$ | 2,4,6-trifluorophenyl |
| 3-CH$_3$,4-CH$_3$ | 2,4,6-trifluorophenyl |
| 3-OCH$_3$,4-OCH$_3$ | 2,4,6-trifluorophenyl |
| 2-F,4-F | 2,4,6-trifluorophenyl |
| 2-F,4-Cl | 2,4,6-trifluorophenyl |
| 4-CH$_3$ | 2-chlorophenyl |
| 4-Cl | 2-chlorophenyl |
| 4-CH$_3$ | 2-fluorophenyl |
| 4-Cl | 2-fluorophenyl |
| 4-CH$_3$ | 2-chloro-6-fluorophenyl |
| 4-CF$_3$ | 2-chloro-6-fluorophenyl |
| 4-Cl | 2-chloro-6-fluorophenyl |
| 4-F | 2-chloro-6-fluorophenyl |
| 4-OCH$_3$ | 2-chloro-6-fluorophenyl |
| 2-Cl,4-Cl | 2-chloro-6-fluorophenyl |
| 3-Cl,4-Cl | 2-chloro-6-fluorophenyl |
| 2-CH$_3$,4-CH$_3$ | 2-chloro-6-fluorophenyl |
| 3-CH$_3$,4-CH$_3$ | 2-chloro-6-fluorophenyl |
| 2-F,4-F | 2-chloro-6-fluorophenyl |
| 2-F,4-Cl | 2-chloro-6-fluorophenyl |
| 4-CH$_3$ | 2,6-difluoro-4-methoxyphenyl |
| 4-CF$_3$ | 2,6-difluoro-4-methoxyphenyl |
| 4-Cl | 2,6-difluoro-4-methoxyphenyl |
| 4-F | 2,6-difluoro-4-methoxyphenyl |
| 4-OCH$_3$ | 2,6-difluoro-4-methoxyphenyl |
| 2-Cl,4-Cl | 2,6-difluoro-4-methoxyphenyl |
| 3-Cl,4-Cl | 2,6-difluoro-4-methoxyphenyl |
| 2-CH$_3$,4-CH$_3$ | 2,6-difluoro-4-methoxyphenyl |
| 3-CH$_3$,4-CH$_3$ | 2,6-difluoro-4-methoxyphenyl |
| 2-F,4-F | 2,6-difluoro-4-methoxyphenyl |
| 2-F,4-Cl | 2,6-difluoro-4-methoxyphenyl |
| 4-CH$_3$ | 2,6-difluoro-4-ethoxyphenyl |
| 4-Cl | 2,6-difluoro-4-ethoxyphenyl |
| 4-CH$_3$ | 2-nitrophenyl |
| 4-Cl | 2-nitrophenyl |
| 4-CH$_3$ | 2-cyanophenyl |
| 4-Cl | 2-cyanophenyl |
| 4-CH$_3$ | 2-methylphenyl |
| 4-Cl | 2-methylphenyl |
| 4-CH$_3$ | 2,6-difluorophenyl |
| 3-CH$_3$ | 2,6-difluorophenyl |
| 2-CH$_3$ | 2,6-difluorophenyl |
| 4-CF$_3$ | 2,6-difluorophenyl |
| 4-Cl | 2,6-difluorophenyl |
| 3-Cl | 2,6-difluorophenyl |
| 2-Cl | 2,6-difluorophenyl |
| 4-F | 2,6-difluorophenyl |
| 4-NO$_2$ | 2,6-difluorophenyl |
| 4-CN | 2,6-difluorophenyl |
| 4-OCH$_3$ | 2,6-difluorophenyl |
| 4-OCF$_3$ | 2,6-difluorophenyl |
| 4-OCHF$_2$ | 2,6-difluorophenyl |
| 4-OCClF$_2$ | 2,6-difluorophenyl |
| 4-OCBrF$_2$ | 2,6-difluorophenyl |
| 4-SCH$_3$ | 2,6-difluorophenyl |
| 4-SCF$_3$ | 2,6-difluorophenyl |
| — | 2,6-difluorophenyl |
| 2-Cl,4-Cl | 2,6-difluorophenyl |
| 3-Cl,4-Cl | 2,6-difluorophenyl |
| 2-Cl,4-CH$_3$ | 2,6-difluorophenyl |

TABLE 1-continued

| (R³)ₘ | Y |
|---|---|
| 3-CH₃,4-CH₃ | 2,6-difluorophenyl |
| 3-OCH₃,4-OCH₃ | 2,6-difluorophenyl |
| 2-F,4-F | 2,6-difluorophenyl |
| 2-F,4-Cl | 2,6-difluorophenyl |
| 4-CH₃ | 2,4-difluorophenyl |
| 4-CF₃ | 2,4-difluorophenyl |
| 4-Cl | 2,4-difluorophenyl |
| 4-F | 2,4-difluorophenyl |
| 4-OCH₃ | 2,4-difluorophenyl |
| 2-Cl,4-Cl | 2,4-difluorophenyl |
| 3-Cl,4-Cl | 2,4-difluorophenyl |
| 2-CH₃,4-CH₃ | 2,4-difluorophenyl |
| 3-CH₃,4-CH₃ | 2,4-difluorophenyl |
| 2-F,4-F | 2,4-difluorophenyl |
| 2-F,4-Cl | 2,4-difluorophenyl |
| 4-CH₃ | 2,3,4-trifluorophenyl |
| 4-Cl | 2,3,4-trifluorophenyl |
| 4-CH₃ | 2,3,5-trifluorophenyl |
| 4-Cl | 2,3,5-trifluorophenyl |
| 4-CH₃ | 2,3,6-trifluorophenyl |
| 4-Cl | 2,3,6-trifluorophenyl |
| 4-CH₃ | 2,4,5-trifluorophenyl |
| 4-Cl | 2,4,5-trifluorophenyl |
| 4-CH₃ | 2,3-difluorophenyl |
| 4-Cl | 2,3-difluorophenyl |
| 4-CH₃ | 2,5-difluorophenyl |
| 4-Cl | 2,5-difluorophenyl |
| 4-CH₃ | 2-(trifluoromethoxy)phenyl |
| 4-Cl | 2-(trifluoromethoxy)phenyl |
| 4-CH₃ | 2-methoxyphenyl |
| 4-Cl | 2-methoxyphenyl |
| 4-Cl | pentafluorophenyl |
| 4-Cl | 4-methoxy-2,3,5,6-tetrafluorophenyl |
| 4-Cl | 4-ethoxy-2,3,5,6-tetrafluorophenyl |
| 4-Cl | 4-cyano-2,3,5,6-tetrafluorophenyl |
| 4-Cl | 4-nitro-2,3,5,6-tetrafluorophenyl |
| 4-Cl | 2,3,5,6-tetrafluorophenyl |
| 4-Cl | 2,6-difluoro-4-cyanophenyl |
| 4-Cl | 2,6-difluoro-4-nitrophenyl |
| 4-Cl | 2,6-difluoro-4-chlorophenyl |
| 4-Cl | 2,6-difluoro-4-(trifluoromethyl)phenyl |
| 4-Cl | 2-fluoro-6-methylphenyl |
| 4-Cl | 2-fluoro-6-nitrophenyl |
| 4-Cl | 2-cyano-6-fluorophenyl |
| 4-Cl | 2-fluoro-6-(trifluoromethyl)phenyl |
| 4-Cl | 2-(difluoromethoxy)-6-fluorophenyl |
| 4-Cl | 2-fluoro-6-(trifluoromethoxy)phenyl |
| 4-Cl | 2-fluoro-6-methoxyphenyl |
| 4-Cl | 2,3-difluoro-6-(trifluoromethyl)phenyl |
| 4-Cl | 2,6-difluoro-3-chlorophenyl |
| 2-F | 2-fluorophenyl |
| 2-Cl | 2-chlorophenyl |
| 2-F,6-F | 2,6-difluorophenyl |
| 2-F,3-F | 2,3-difluorophenyl |
| 2-F,5-F | 2,5-difluorophenyl |

In the table, "—" means that m is 0.

Next, specific examples of the intermediate of the compound of the present invention will be shown below:

The compound represented by the formula (2-a);

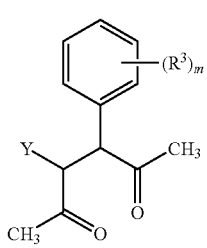

(2-a)

The compound represented by the formula (3-a);

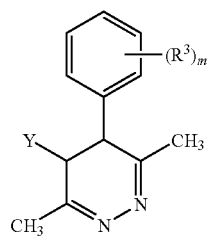

(3-a)

The compound represented by the formula (4-a);

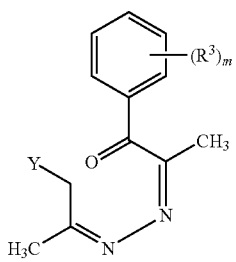

(4-a)

The compound represented by the formula (5-a);

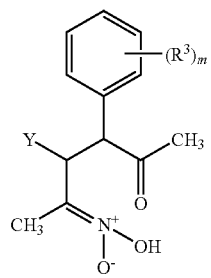

(5-a)

In the formula (2-a), formula (3-a), formula (4-a) and formula (5-a), (R³)ₘ and Y represent one combination of substituents shown in Table 2.

TABLE 2

| (R³)ₘ | Y |
|---|---|
| 4-CH₃ | 2-(trifluoromethyl)phenyl |
| 4-Cl | 2-(trifluoromethyl)phenyl |
| 4-CH₃ | 2-(difluoromethoxy)phenyl |
| 4-Cl | 2-(difluoromethoxy)phenyl |
| 4-CH₃ | 2,4,6-trifluorophenyl |
| 3-CH₃ | 2,4,6-trifluorophenyl |
| 2-CH₃ | 2,4,6-trifluorophenyl |
| 4-CF₃ | 2,4,6-trifluorophenyl |
| 4-Cl | 2,4,6-trifluorophenyl |
| 3-Cl | 2,4,6-trifluorophenyl |
| 2-Cl | 2,4,6-trifluorophenyl |
| 4-F | 2,4,6-trifluorophenyl |
| 4-NO₂ | 2,4,6-trifluorophenyl |
| 4-CN | 2,4,6-trifluorophenyl |
| 4-OCH₃ | 2,4,6-trifluorophenyl |
| 4-OCF₃ | 2,4,6-trifluorophenyl |
| 4-OCHF₂ | 2,4,6-trifluorophenyl |
| 4-OCClF₂ | 2,4,6-trifluorophenyl |

TABLE 2-continued

| $(R^3)_m$ | Y |
|---|---|
| 4-OCBrF$_2$ | 2,4,6-trifluorophenyl |
| 4-SCH$_3$ | 2,4,6-trifluorophenyl |
| 4-SCF$_3$ | 2,4,6-trifluorophenyl |
| — | 2,4,6-trifluorophenyl |
| 2-Cl,4-Cl | 2,4,6-trifluorophenyl |
| 3-Cl,4-Cl | 2,4,6-trifluorophenyl |
| 2-CH$_3$,4-CH$_3$ | 2,4,6-trifluorophenyl |
| 3-CH$_3$,4-CH$_3$ | 2,4,6-trifluorophenyl |
| 3-OCH$_3$,4-OCH$_3$ | 2,4,6-trifluorophenyl |
| 2-F,4-F | 2,4,6-trifluorophenyl |
| 2-F,4-Cl | 2,4,6-trifluorophenyl |
| 4-CH$_3$ | 2-chlorophenyl |
| 4-Cl | 2-chlorophenyl |
| 4-CH$_3$ | 2-fluorophenyl |
| 4-Cl | 2-fluorophenyl |
| 4-CH$_3$ | 2-chloro-6-fluorophenyl |
| 4-CF$_3$ | 2-chloro-6-fluorophenyl |
| 4-Cl | 2-chloro-6-fluorophenyl |
| 4-F | 2-chloro-6-fluorophenyl |
| 4-OCH$_3$ | 2-chloro-6-fluorophenyl |
| 2-Cl,4-Cl | 2-chloro-6-fluorophenyl |
| 3-Cl,4-Cl | 2-chloro-6-fluorophenyl |
| 2-CH$_3$,4-CH$_3$ | 2-chloro-6-fluorophenyl |
| 3-CH$_3$,4-CH$_3$ | 2-chloro-6-fluorophenyl |
| 2-F,4-F | 2-chloro-6-fluorophenyl |
| 2-F,4-Cl | 2-chloro-6-fluorophenyl |
| 4-CH$_3$ | 2,6-difluoro-4-methoxyphenyl |
| 4-CF$_3$ | 2,6-difluoro-4-methoxyphenyl |
| 4-Cl | 2,6-difluoro-4-methoxyphenyl |
| 4-F | 2,6-difluoro-4-methoxyphenyl |
| 4-OCH$_3$ | 2,6-difluoro-4-methoxyphenyl |
| 2-Cl,4-Cl | 2,6-difluoro-4-methoxyphenyl |
| 3-Cl,4-Cl | 2,6-difluoro-4-methoxyphenyl |
| 2-CH$_3$,4-CH$_3$ | 2,6-difluoro-4-methoxyphenyl |
| 3-CH$_3$,4-CH$_3$ | 2,6-difluoro-4-methoxyphenyl |
| 2-F,4-F | 2,6-difluoro-4-methoxyphenyl |
| 2-F,4-Cl | 2,6-difluoro-4-methoxyphenyl |
| 4-CH$_3$ | 2,6-difluoro-4-ethoxyphenyl |
| 4-Cl | 2,6-difluoro-4-ethoxyphenyl |
| 4-CH$_3$ | 2-nitrophenyl |
| 4-Cl | 2-nitrophenyl |
| 4-CH$_3$ | 2-cyanophenyl |
| 4-Cl | 2-cyanophenyl |
| 4-CH$_3$ | 2-methylphenyl |
| 4-Cl | 2-methylphenyl |
| 4-CH$_3$ | 2,6-difluorophenyl |
| 3-CH$_3$ | 2,6-difluorophenyl |
| 2-CH$_3$ | 2,6-difluorophenyl |
| 4-CF$_3$ | 2,6-difluorophenyl |
| 4-Cl | 2,6-difluorophenyl |
| 3-Cl | 2,6-difluorophenyl |
| 2-Cl | 2,6-difluorophenyl |
| 4-F | 2,6-difluorophenyl |
| 4-NO$_2$ | 2,6-difluorophenyl |
| 4-CN | 2,6-difluorophenyl |
| 4-OCH$_3$ | 2,6-difluorophenyl |
| 4-OCF$_3$ | 2,6-difluorophenyl |
| 4-OCHF$_2$ | 2,6-difluorophenyl |
| 4-OCClF$_2$ | 2,6-difluorophenyl |
| 4-OCBrF$_2$ | 2,6-difluorophenyl |
| 4-SCH$_3$ | 2,6-difluorophenyl |
| 4-SCF$_3$ | 2,6-difluorophenyl |
| — | 2,6-difluorophenyl |
| 2-Cl,4-Cl | 2,6-difluorophenyl |
| 3-Cl,4-Cl | 2,6-difluorophenyl |
| 2-Cl,4-CH$_3$ | 2,6-difluorophenyl |
| 3-CH$_3$,4-CH$_3$ | 2,6-difluorophenyl |
| 3-OCH$_3$,4-OCH$_3$ | 2,6-difluorophenyl |
| 2-F,4-F | 2,6-difluorophenyl |
| 2-F,4-Cl | 2,6-difluorophenyl |
| 4-CH$_3$ | 2,4-difluorophenyl |
| 4-CF$_3$ | 2,4-difluorophenyl |
| 4-Cl | 2,4-difluorophenyl |
| 4-F | 2,4-difluorophenyl |
| 4-OCH$_3$ | 2,4-difluorophenyl |
| 2-Cl,4-Cl | 2,4-difluorophenyl |
| 3-Cl,4-Cl | 2,4-difluorophenyl |

TABLE 2-continued

| $(R^3)_m$ | Y |
|---|---|
| 2-CH$_3$,4-CH$_3$ | 2,4-difluorophenyl |
| 3-CH$_3$,4-CH$_3$ | 2,4-difluorophenyl |
| 2-F,4-F | 2,4-difluorophenyl |
| 2-F,4-Cl | 2,4-difluorophenyl |
| 4-CH$_3$ | 2,3,4-trifluorophenyl |
| 4-Cl | 2,3,4-trifluorophenyl |
| 4-CH$_3$ | 2,3,5-trifluorophenyl |
| 4-Cl | 2,3,5-trifluorophenyl |
| 4-CH$_3$ | 2,3,6-trifluorophenyl |
| 4-Cl | 2,3,6-trifluorophenyl |
| 4-CH$_3$ | 2,4,5-trifluorophenyl |
| 4-Cl | 2,4,5-trifluorophenyl |
| 4-CH$_3$ | 2,3-difluorophenyl |
| 4-Cl | 2,3-difluorophenyl |
| 4-CH$_3$ | 2,5-difluorophenyl |
| 4-Cl | 2,5-difluorophenyl |
| 4-CH$_3$ | 2-(trifluoromethoxy)phenyl |
| 4-Cl | 2-(trifluoromethoxy)phenyl |
| 4-CH$_3$ | 2-methoxyphenyl |
| 4-Cl | 2-methoxyphenyl |
| 4-Cl | pentafluorophenyl |
| 4-Cl | 4-methoxy-2,3,5,6-tetrafluorophenyl |
| 4-Cl | 4-ethoxy-2,3,5,6-tetrafluorophenyl |
| 4-Cl | 4-cyano-2,3,5,6-tetrafluorophenyl |
| 4-Cl | 4-nitro-2,3,5,6-tetrafluorophenyl |
| 4-Cl | 2,3,5,6-tetrafluorophenyl |
| 4-Cl | 2,6-difluoro-4-cyanophenyl |
| 4-Cl | 2,6-difluoro-4-nitrophenyl |
| 4-Cl | 2,6-difluoro-4-chlorophenyl |
| 4-Cl | 2,6-difluoro-4-(trifluoromethyl)phenyl |
| 4-Cl | 2-fluoro-6-methylphenyl |
| 4-Cl | 2-fluoro-6-nitrophenyl |
| 4-Cl | 2-cyano-6-fluorophenyl |
| 4-Cl | 2-fluoro-6-(trifluoromethyl)phenyl |
| 4-Cl | 2-(difluoromethoxy)-6-fluorophenyl |
| 4-Cl | 2-fluoro-6-(trifluoromethoxy)phenyl |
| 4-Cl | 2-fluoro-6-methoxyphenyl |
| 4-Cl | 2,3-difluoro-6-(trifluoromethyl)phenyl |
| 4-Cl | 2,6-difluoro-3-chlorophenyl |
| 2-F | 2-fluorophenyl |
| 2-Cl | 2-chlorophenyl |
| 2-F,6-F | 2,6-difluorophenyl |
| 2-F,3-F | 2,3-difluorophenyl |
| 2-F,5-F | 2,5-difluorophenyl |

In the table, "—" means that m is 0.

The compound represented by the formula (7-a);

(7-a)

The compound represented by the formula (9-a);

(9-a)

In the formula (8-a) and formula (9-a), Y represents one of substituent shown in Table 3.

TABLE 3

| Y |
|---|
| 2,4,6-trifluorophenyl |
| 2-chloro-6-fluorophenyl |
| 2,6-difluoro-4-methoxyphenyl |
| 2,6-difluoro-4-ethoxyphenyl |
| 2,6-difluorophenyl |
| 2,4-difluorophenyl |
| 2,3,4-trifluorophenyl |
| 2,3,5-trifluorophenyl |
| 2,3,6-trifluorophenyl |
| 2,4,5-trifluorophenyl |
| 2,3-difluorophenyl |
| 2,5-difluorophenyl |
| 2-chlorophenyl |
| 2-fluorophenyl |
| 2-nitrophenyl |
| 2-cyanophenyl |
| 2-methylphenyl |
| 2-(trifluoromethyl)phenyl |
| 2-(difluoromethoxy)phenyl |
| 2-(trifluoromethoxy)phenyl |
| 2-methoxyphenyl |
| pentafluorophenyl |
| 4-methoxy-2,3,5,6-tetrafluorophenyl |
| 4-ethoxy-2,3,5,6-tetrafluorophenyl |
| 4-cyano-2,3,5,6-tetrafluorophenyl |
| 4-nitro-2,3,5,6-tetrafluorophenyl |
| 2,3,5,6-tetrafluorophenyl |
| 2,6-difluoro-4-cyanophenyl |
| 2,6-difluoro-4-nitrophenyl |
| 2,6-difluoro-4-chlorophenyl |
| 2,6-difluoro-4-(trifluoromethyl)phenyl |
| 2-fluoro-6-methylphenyl |
| 2-fluoro-6-nitrophenyl |
| 2-cyano-6-fluorophenyl |
| 2-fluoro-6-(trifluoromethyl)phenyl |
| 2-(difluoromethoxy)-6-fluorophenyl |
| 2-fluoro-6-(trifluoromethoxy)phenyl |
| 2-fluoro-6-methoxyphenyl |
| 2,3-difluoro-6-(trifluoromethyl)phenyl |
| 2,6-difluoro-3-chlorophenyl |

The compound represented by the formula (6-a);

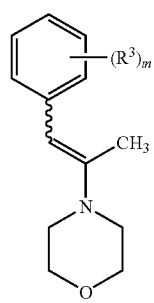

(6-a)

The compound represented by the formula (8-a);

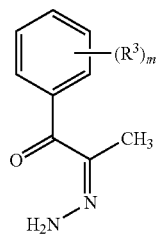

(8-a)

The compound represented by the formula (10-a);

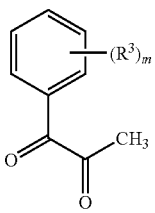

(10-a)

In the formula (6-a), formula (8-a) and formula (10-a), $(R^3)_m$ represents one of substituent shown in Table 4.

TABLE 4

| $(R^3)_m$ |
|---|
| 4-CH$_3$ |
| 3-CH$_3$ |
| 2-CH$_3$ |
| 4-CF$_3$ |
| 4-Cl |
| 3-Cl |
| 2-Cl |
| 4-F |
| 4-NO$_2$ |
| 4-CN |
| 4-OCH$_3$ |
| 4-OCF$_3$ |
| 4-OCHF$_2$ |
| 4-OCClF$_2$ |
| 4-OCBrF$_2$ |
| 4-SCH$_3$ |
| 4-SCF$_3$ |
| — |
| 2-Cl,4-Cl |
| 3-Cl,4-Cl |
| 2-CH$_3$,4-CH$_3$ |
| 3-CH$_3$,4-CH$_3$ |
| 3-OCH$_3$,4-OCH$_3$ |
| 2-F,4-F |
| 2-F,4-Cl |

In the table, "—" means that m is 0.

The plant diseases to be controlled by the present compound will be exemplified below.

*Pyricularia oryzae, Cochliobolus miyabeanus* and *Rhizoctonia solani* of rice;

*Erysiphe graminis, Gibberella zeae, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septo-*

*ria tritici* and *Leptosphaeria nodorum*, of wheat and barley; *Diaporthe citri, Elsinoe fawcetti, Penicillium digitatum* and *P. italicum* of citrus;

*Sclerotinia mali, Valsa mali, Podosphaera leucotricha, Alternaria mali* and *Venturia inaequalis* of apple;

*Venturia nashicola, V. pirina, Alternaria kikuchiana* and *Gymnosporangium haraeanum* of pear;

*Sclerotinia cinerea, Cladosporium carpophilum* and *Phomopsis* sp. of peach;

*Elsinoe ampelina, Glomerella cingulata, Uncinula necator, Phakopsora ampelopsidis, Guignardia bidwellii* and *Plasmopara viticola*, of grape;

*Gloeosporium kaki, Cercospora kaki* and *Mycosphaerella nawae* of Japanese persimmon;

*Colletotrichum lagenarium, Sphaerotheca fuliginea, Mycosphaerella melonis, Fusarium oxysporum, Pseudoperonospora cubensis Phytophthora* sp. and *Pythium* sp. of cucurbit;

*Alternaria solani, Cladosporium fulvum* and *Phytophthora infestans* of tomato;

*Phomopsis vexans* and *Erysiphe cichoracearum*, of eggplant; *Alternaria japonica* and *Cercosporella brassicae* of Cruciferae vegetables;

*Puccinia allii* of green onion; *Cercospora kikuchii, Elsinoe glycines* and *Diaporthe phaseolorum* var. *sojae* of soybean; *Colletotrichum lindemthianum* of kidney bean;

*Cercospora personata* and *Cercospora arachidicola* of peanut; *Erysiphe pisi* of pea;

*Alternaria solani* and *Phytophthora infestans* of potato; *Sphaerotheca humuli* of strawberry;

*Exobasidium reticulatum* and *Elsinoe leucospila* of tea; *Alternaria longipes, Erysiphe cichoracearum, Colletotrichum tabacum, Peronospora tabacina* and *Phytophthora nicotianae* of tobacco; *Cercospora beticola* of sugar beet;

*Diplocarpon rosae* and *Sphaerotheca pannosa* of rose; *Septoria chrysanthemi-indici* and *Puccinia horiana* of chrysanthemum;

*Botrytis cinerea* and *Sclerotinia sclerotiorum* of various crops; *Alternaria brassicicola* of radish;

and *Sclerotinia homeocarpa* and *Rhizoctonia solani* of turf.

Fungicidal effect may be shown by treating the compound of the present invention as it is to plants or soils. But, usually, it is used by the form of composition comprising the compound of the present invention and a carrier. Namely, the fungicidal composition of the present invention is formulated to an emulsifiable concentrate, a wettable powder, a water dispersible granule, a flowable, a dust, a granule and the like by mixing the compound of the present invention and a solid carrier and/or a liquid carrier and, if necessary, adding other adjuvant for formulation such as surfactant.

These formulations usually contain 0.1 to 90% by weight of the compound of the present invention.

Solid carriers used for formulation include, for example, fine powders or granules of minerals such as kaolin clay, attapulgite clay, bentonite, montmorillonite, terra alba, pyrophyllite, talc, diatomaceous earth, calcite and the like; natural organic substances such as corncob powder, walnut shell powder and the like; synthetic organic substances such as urea and the like; salts such as calcium carbonate, ammonium sulfate and the like; synthetic inorganic substances such as synthetic hydrous silicon oxide and the like. Liquid carriers include, for example, aromatic hydrocarbons such as xylene, alkylbenzene, methylnaphthalene and the like; alcohols such as 2-propanol, ethylene glycol, propylene glycol, cellosolve and the like; ketones such as acetone, cyclohexanone, isophorone and the like; vegetable oils such as soybean oil, cottonseed oil and the like; aliphatic hydrocarbons, esters, dimethylsulfoxide, acetonitrile and water.

Surfactants include, for example, anionic surfactants such as alkylsulfuric acid ester salt, alkylarylsulfonic acid salt, dialkylsulfosuccinic acid salt, polyoxyethylenealkylaryletherphosphoric acid ester salt, lignin sulfonic acid salt, naphthalenesulfonate polycondensed with formaldehyde and the like; and nonionic surfactants such as polyoxyethylenealkylarylether, polyoxyethylenealkylpolyoxypropylene block copolymer, sorbitan fatty acid ester and the like.

Another adjuvant for formulation includes, for example, water-soluble polymers such as polyvinylalcohol, polyvinylpyrrolidone and the like; Arabian gum; alginic acid and its salt thereof; polysaccharides such as CMC (carboxymethylcellulose), xanthan gum and the like; inorganic substances such as aluminum magnesium silicate, alumina sol and the like; and preservatives, colorants, PAP (isopropyl acidic phosphate), stabilizing agents such as BHT and the like.

By applying the fungicidal composition of the present invention to foliage of plants, said plants can be protected from plant diseases; and by applying the fungicidal composition of the present invention to soils, the plants grown on said soils can be protected from plant diseases. Namely, the fungicidal composition of the present invention is usually used for a method for controlling plant diseases comprising a step applying an effective amount of the fungicidal composition of the present invention to plants or soils growing the plants.

When the fungicidal composition of the present invention is applied to plants or when the fungicidal composition of the present invention is applied to soil, the application amount thereof, which may be varied with a kind of control-object plants, a kind of control-object diseases, an infestation level of control-object diseases, formulation types, application timings, weather conditions and the like, is usually 1 to 5,000 g, preferably 5 to 1,000 g, of the compound of the present invention per 10,000 m$^2$.

Emulsifiable concentrate, wettable powder, flowable and the like are usually sprayed after diluted with water. In this case, the concentration of the compound of the present invention is usually in the range of from 0.0001 to 3% by weight, preferably from 0.0005 to 1% by weight. Dust, granule and the like are usually directly applied without dilution.

The fungicidal composition of the present invention can be also applied in treatment methods of seed disinfection. The methods include, for example, a method to soak seeds of a plant in the fungicidal composition of the present invention which prepared in 1 to 1,000 ppm in terms of concentration of the compound of the present invention, a method to spray or coat seeds of a plant with the fungicidal composition of the present invention which prepared in 1 to 1,000 ppm in terms of concentration of the compound of the present invention, and a method to coat seeds of a plant with the fungicidal composition of the present invention which is formulated to dust.

The method for controlling plant diseases of the present invention is usually performed by applying effective amount of the fungicidal composition of the present invention to a plant or a soil growing the plant in which infection is predictable.

The fungicidal composition of the present invention is usually used as a fungicide controlling plant diseases for agriculture or gardening, that is, as an agent controlling plant diseases to control plant diseases on plowed fields, paddy fields, orchards, tea fields, pastures, turf and the like.

The fungicidal composition of the present invention may be used together with other fungicides, insecticides, acaricides, nematocides, herbicides, plant growth regulators and/or fertilizers.

Examples of the active ingredient of the fungicides include azole fungicidal compounds such as propiconazole, triadimenol, prochloraz, penconazole, tebuconazole, flusilazole, diniconazole, bromuconazole, epoxyconazole, difenoconazole, cyproconazole, metconazole, triflumizole, tetraconazole, myclobutanil, fenbuconazole, hexaconazole, fluquinconazole, triticonazole, bitertanol, imazalil, flutriafol and so on; cyclic amine fungicidal compounds such as fenpropimorph, tridemorph, fenpropidin and so on; benzimidazole fungicidal compounds such as carbendazim, benomyl, thiabendazole, thiophanate-methyl and so on; procymidone; cyprodinil; pyrimethanil; diethofencarb; thiuram; fluazinam; mancozeb; iprodione; vinclozolin; chlorothalonil; captan; mepanipyrim; fenpiclonil; fludioxonil; dichlorfluanid; folpet; kresoxim-methyl; azoxystrobin; trifloxystrobin; picoxystrobin; pyraclostrobin; N-methyl-α-methoxyimino-2-[(2,5-dimethylphenoxy)methyl]phenylacetamide; spiroxamine; quinixyfen; fenhexamide; famoxadone; fenamidone; iprovalicarb; benthiavalicarb; cyazofamid; boscalid; metrafenone and cyflufenamid.

The present invention will be illustrated further in detail by production examples, formulation examples, test examples and the like below, but the present invention is not limited to these examples.

First, production examples of the compound of the present invention will be described.

PRODUCTION EXAMPLE 1

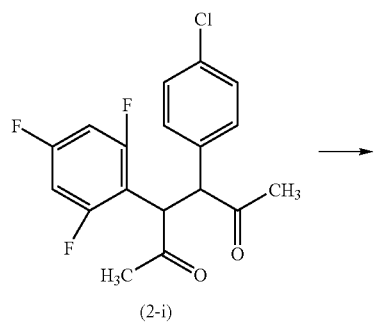

(2-i)

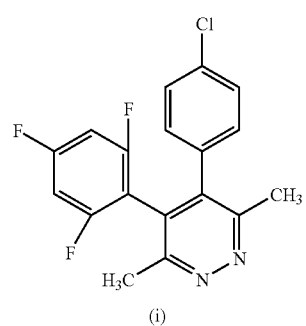

(i)

0.39 g of the compound represented by the formula (2-i), 56.0 mg of hydrazine monohydrate and 2 ml of ethanol were mixed and stirred at room temperature for 4 hours. To the reaction mixture was added 0.33 g of platinum oxide (PtO$_2$), and the mixture was stirred at room temperature for one day, at 60° C. overnight, and at heat-reflux for 4 hours. After that, the reaction mixture was allowed to cool to room temperature, and filtered through Celite. The filtrate was concentrated under reduced pressure. The residue is subjected to silica gel column chromatography to obtain 0.11 g of 4-(4-chlorophenyl)-2,6-dimethyl-5-(2,4,6-trifluorophenyl)pyridazine (hereinafter, referred to as compound (i) of the present invention).

$^1$H-NMR (CDCl$_3$, TMS) δ (ppm): 2.51 (6H, s), 6.61 (2H, t, J=7.0 Hz), 6.99 (2H, d, J=8.3 Hz), 7.28 (2H, d, J=8.3 Hz)

PRODUCTION EXAMPLE 2

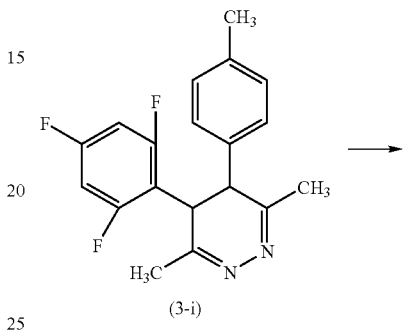

(3-i)

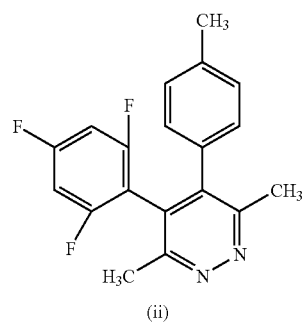

(ii)

1.09 g of the crude compound represented by the formula (3-i), 1.52 g of lead dioxide (PbO$_2$) and 10 ml of ethanol were mixed and stirred at 60° C. for 6 hours. After that, the reaction mixture was allowed to cool to room temperature, and filtered through Celite. The filtrate was concentrated under reduced pressure, and the residue was subjected to silica gel column chromatography to obtain 0.84 g of 2,6-dimethyl-4-(4-methylphenyl)-5-(2,4,6-trifluorophenyl)pyridazine (hereinafter, referred to as compound (II) of the present invention).

$^1$H-NMR (CDCl$_3$, TMS) δ (ppm): 2.31 (3H, s), 2.50 (3H, s), 2.51 (3H, s), 6.58 (2H, t, J=7.0 Hz), 6.91 (2H, d, J=8.0 Hz), 7.08 (2H, d, J=8.0 Hz)

PRODUCTION EXAMPLE 3

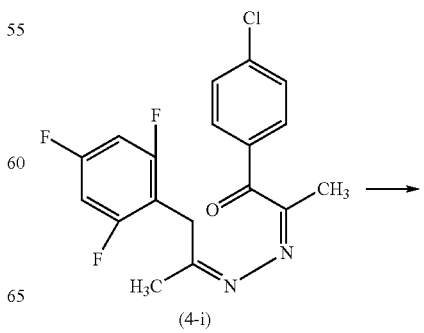

(4-i)

$^1$H-NMR (CDCl$_3$, TMS)$_6$ (ppm): 2.51 (6H, s), 6.58 (2H, t, J=8.4 Hz), 7.0-7.1 (2H, m), 7.2-7.35 (3H, m)

PRODUCTION EXAMPLE 5

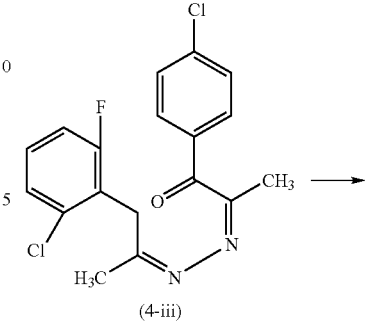
(4-iii)

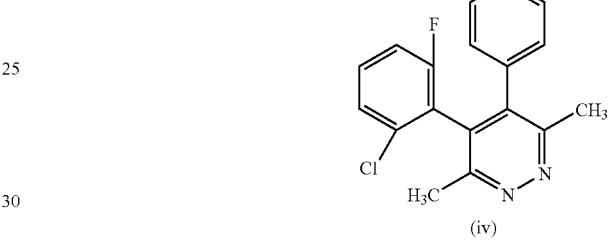
(iv)

In 10 ml of ethanol was dissolved 1.34 g the crude compound represented by the formula (4-iii), to which 30 mg of powdery potassium hydroxide was added, and the mixture was stirred at heat-reflux under nitrogen atmosphere for 3 hours. After that, to the mixture was added 200 mg of powdery potassium hydroxide, which was stirred at heat-reflux under nitrogen atmosphere for 4 hours. The reaction mixture was allowed to cool to room temperature and poured into a mixture of brine and ice, which was extracted with ethyl acetate. The organic layer was washed with saturated brine, dried and concentrated under reduced pressure. The residue was subjected to silica gel column chromatography to obtain 0.18 g of 4-(2-chloro-6-fluorophenyl)-5-(4-chlorophenyl)-2,6-dimethyl pyridazine (hereinafter, referred to as compound (iv) of the present invention).

$^1$H-NMR (CDCl$_3$, TMS) δ (ppm): 2.46 (3H, s), 2.51 (3H, s), 6.9-7.0 (1H, m), 7.0-7.1 (2H, m), 7.1-7.3 (4H, m)

PRODUCTION EXAMPLE 6

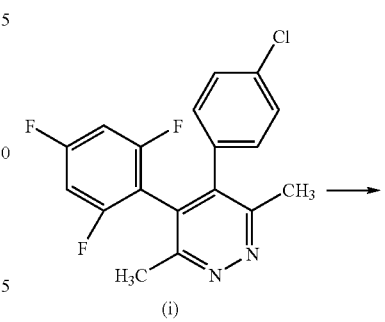
(i)

-continued

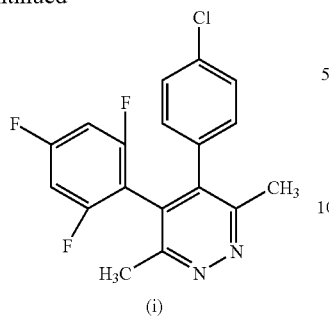
(i)

In 30 ml of tert-butanol was dissolved 3.52 g of the crude compound represented by the formula (4-i), to which 0.67 g of powdery potassium hydroxide was added, and the mixture was stirred at heat-reflux under nitrogen atmosphere for 4 hours. The reaction mixture was allowed to cool to room temperature and poured into a mixture of brine and ice, which was extracted with ethylacetate. The organic layer was washed with saturated brine, dried and concentrated under reduced pressure. The residue was subjected to silica gel column chromatography to obtain 0.54 g of 4-(4-chlorophenyl)-2,6-dimethyl-5-(2,4,6-trifluorophenyl)pyridazine (the compound (i) of the present invention).

PRODUCTION EXAMPLE 4

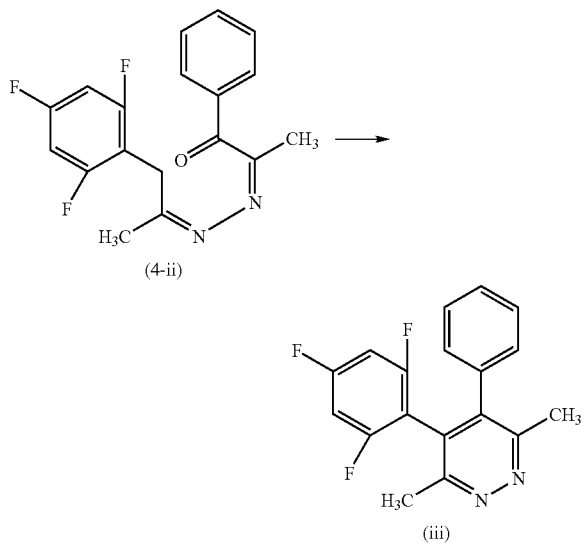
(4-ii)

(iii)

In 20 ml of tert-butanol was dissolved 2.75 g of the crude compound represented by the formula (4-ii), to which 0.56 g of powdery potassium hydroxide was added, and the mixture was stirred at heat-reflux under nitrogen atmosphere for 4 hours. The reaction mixture was allowed to cool to room temperature and poured into a mixture of brine and ice, which was extracted with ethylacetate. The organic layer was washed with saturated brine, dried and concentrated under reduced pressure. The residue was subjected to silica gel column chromatography to obtain 0.36 g of 2,6-dimethyl-4-phenyl-5-(2,4,6-trifluorophenyl)pyridazine (hereinafter, referred to as compound (iii) of the present invention).

-continued

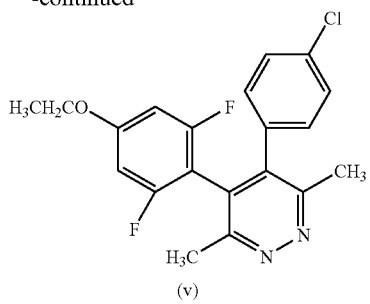

(v)

In 6 ml of ethanol was dissolved 174 mg of compound (i) of the present invention, to which 1.70 g of sodium ethylate (20% ethanol solution), and the mixture was stirred at heat-reflux under nitrogen atmosphere for 2 hours. The reaction mixture was allowed to cool to room temperature and poured into a mixture of brine and ice, which was extracted with ethyl acetate. The organic layer was washed with saturated brine, dried and concentrated under reduced pressure. The residue was subjected to silica gel column chromatography to obtain 0.13 g of 4-(4-chlorophenyl)-5-(4-ethoxy-2,6-difluorophenyl)-2,6-dimethylpyridazine (hereinafter, referred to as compound (v) of the present invention).

$^1$H-NMR (CDCl$_3$, TMS) δ (ppm): 1.39 (3H, t, J=8 Hz), 2.49 (3H, s), 2.51 (3H, s), 3.95 (2H, q, J=8 Hz), 6.3-6.4 (2H, m), 7.00 (2H, d, J=8 Hz), 7.27 (2H, d, J=8 Hz)

PRODUCTION EXAMPLE 7

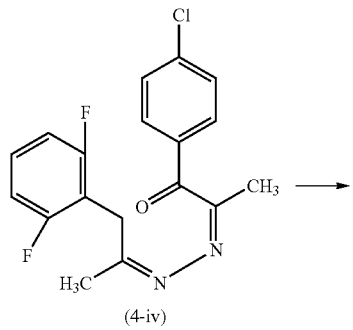

(4-iv)

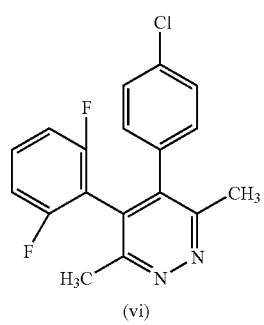

(vi)

In 25 ml of ethanol was dissolved 3.44 g of the crude compound represented by the formula (4-iv), to which 0.79 g of powdery potassium hydroxide was added, and the mixture was stirred at heat-reflux under nitrogen atmosphere for 3 hours. The reaction mixture was allowed to cool to room temperature and poured into a mixture of brine and ice, which was extracted with ethyl acetate. The organic layer was washed with saturated brine, dried and concentrated under reduced pressure. The residue was subjected to silica gel column chromatography to obtain 0.58 g of 4-(4-chlorophenyl)-5-(2,6-difluorophenyl)-2,6-dimethylpyridazine (hereinafter, referred to as compound (vi) of the present invention).

$^1$H-NMR (CDCl$_3$, TMS) δ (ppm): 2.51 (6H, s), 6.83 (2H, t, J=7.6 Hz), 6.99 (2H, d, J=8.4 Hz), 7.2-7.4 (3H)

PRODUCTION EXAMPLE 8

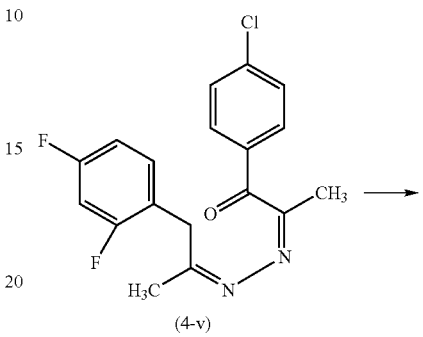

(4-v)

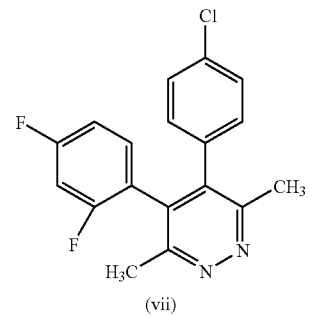

(vii)

In 25 ml of tert-butanol was dissolved 3.64 g of the crude compound represented by the formula (4-v), to which 0.79 g of powdery potassium hydroxide was added, and the mixture was stirred at heat-reflux under nitrogen atmosphere for 3 hours. The reaction mixture was allowed to cool to room temperature and poured into a mixture of brine and ice, which was extracted with ethyl acetate. The organic layer was washed with saturated brine, dried and concentrated under reduced pressure. The residue was subjected to silica gel column chromatography to obtain 0.72 g of 4-(4-chlorophenyl)-5-(2,4-difluorophenyl)-2,6-dimethylpyridazine (hereinafter, referred to as compound (vii) of the present invention).

$^1$H-NMR (CDCl$_3$, TMS) δ (ppm): 2.49 (3H, s), 2.50 (3H, s), 6.7-6.9 (3H), 6.94 (2H, d, J=8.0 Hz), 7.25 (2H, d, J=8.0 Hz)

PRODUCTION EXAMPLE 9

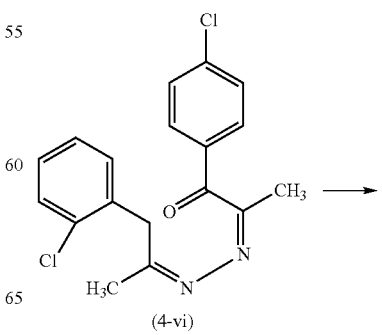

(4-vi)

-continued

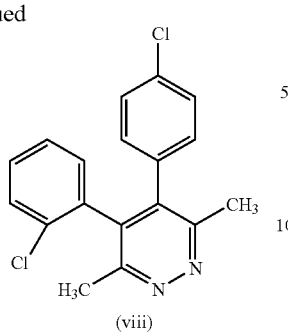

(viii)

In 25 ml of ethanol was dissolved 3.71 g of the crude compound represented by the formula (4-vi), to which 0.79 g of powdery potassium hydroxide was added, and the mixture was stirred at heat-reflux under nitrogen atmosphere for 3 hours. The reaction mixture was allowed to cool to room temperature and poured into a mixture of brine and ice, which was extracted with ethyl acetate. The organic layer was washed with saturated brine, dried and concentrated under reduced pressure. The residue was subjected to silica gel column chromatography to obtain 0.58 g of 4-(4-chlorophenyl)-5-(2-chlorophenyl)-2,6-dimethylpyridazine (hereinafter, referred to as compound (viii) of the present invention).

$^1$H-NMR (CDCl$_3$, TMS) δ (ppm): 2.44 (3H, s), 2.51 (3H, s), 6.90 (1H, dd, J=7.6 Hz, J=1.6 Hz), 6.95-7.05 (2H, br), 7.15 (2H, td, J=7.6 Hz, J=1.6 Hz), 7.2-7.4 (3H)

PRODUCTION EXAMPLE 10

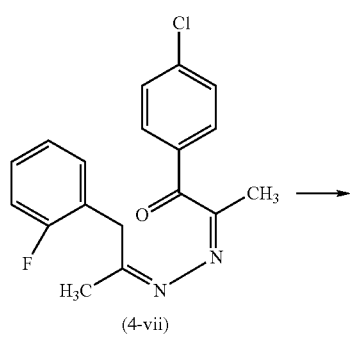

In 25 ml of ethanol was dissolved 3.30 g of the crude compound represented by the formula (4-vii), to which 0.79 g of powdery potassium hydroxide was added, and the mixture was stirred at heat-reflux under nitrogen atmosphere for 4 hours. The reaction mixture was allowed to cool to room temperature and poured into a mixture of brine and ice, which was extracted with ethyl acetate. The organic layer was washed with saturated brine, dried and concentrated under reduced pressure. The residue was subjected to silica gel column chromatography to obtain 0.42 g of 4-(4-chlorophenyl)-2,6-dimethyl-5-(2-fluorophenyl)pyridazine (hereinafter, referred to as compound (ix) of the present invention).

$^1$H-NMR (CDCl$_3$, TMS) δ (ppm): 2.49 (3H, s), 2.51 (3H, s), 6.85-7.05 (5H) 7.2-7.3 (3H)

PRODUCTION EXAMPLE 11

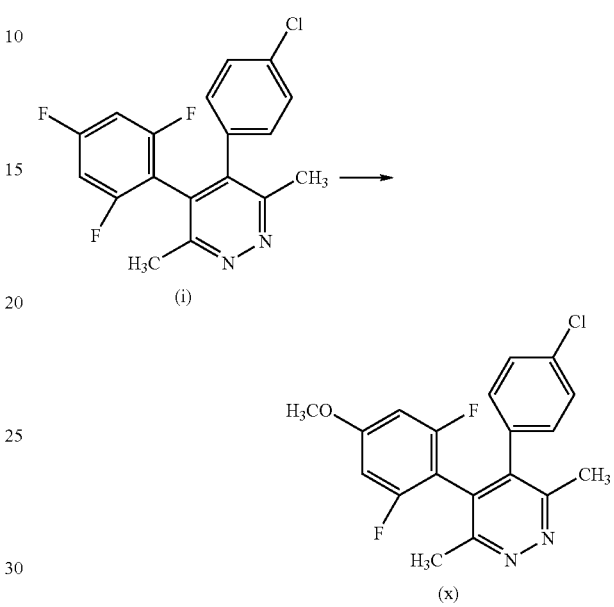

In 6 ml methanol was dissolved 174 mg of compound (i) of the present invention, to which 0.96 g of sodium methylate (28% methanol solution) was added, and the mixture was stirred at heat-reflux under nitrogen atmosphere for 3 hours.

To the mixture was added 0.96 g of sodium methylate (28% methanol solution), which was stirred at heat-reflux under nitrogen atmosphere for 8.5 hours. The reaction mixture was allowed to cool to room temperature and poured into a mixture of brine and ice, which was extracted with ethyl acetate. The organic layer was washed with saturated brine, dried and concentrated under reduced pressure to obtain 147 mg of 4-(4-chlorophenyl)-5-(2,6-difluoro-4-methoxyphenyl)-2,6-dimethylpyridazine (hereinafter, referred to as compound (x) of the present invention).

$^1$H-NMR (CDCl$_3$, TMS) δ (ppm): 2.50 (3H, s), 2.51 (3H, s), 3.76 (3H, s), 6.35-6.4 (2H, m), 7.00 (2H, d, J=8 Hz), 7.27 (2H, d, J=8 Hz)

Next, the production of intermediate compounds of the present compounds will be descried in the following Reference Production Examples.

REFERENCE PRODUCTION EXAMPLE 1

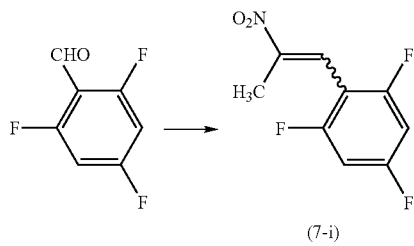

A mixture of 4.80 g of 2,4,6-trifluorobenzaldehyde, 0.72 g of ammonium acetate and 19.34 g of nitroethane was heated to reflux under nitrogen atmosphere for 7 hours. The reaction mixture was allowed to cool to room temperature and concentrated under reduced pressure. To the residue was added ethyl acetate, which was washed with saturated brine twice. After the organic layer was dried over anhydrous sodium sulfate, it was concentrated under reduced pressure, and the residue was subjected to silica gel column chromatography to obtain 4.80 g of the compound represented by the formula (7-i).

$^1$H-NMR (CDCl$_3$, TMS) δ (ppm): 2.23 (3H, s), 6.7-6.8 (2H, m), 7.77 (1H, s)

REFERENCE PRODUCTION EXAMPLE 2

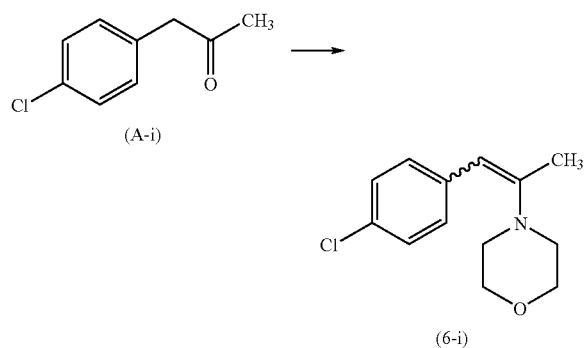

A mixture of 3.45 g of the compound represented by the formula (A-i), 6.24 g of morpholine dissolved in 20 ml of toluene and 100 ml of toluene was allowed to cool to 0° C. under nitrogen atmosphere. To the mixture was added dropwise a mixed solution of 10 ml of toluene and 11.5 ml of titanium tetrachloride (1.0 M toluene solution) over 50 minutes, and the mixture was stirred at room temperature overnight. The reaction mixture was filtered through Celite. The filtrate was concentrated under reduced pressure. To the residue was added hexane, and generated solid was collected by filtration. The solid was washed with hexane twice and dried under reduced pressure to obtain 3.46 g of the compound represented by the formula (6-i).

$^1$H-NMR (CDCl$_3$, TMS) δ (ppm): 1.95 (3H, s), 3.00 (4H, t, J=4.8 Hz), 3.78 (4H, t, J=4.8 Hz), 5.48 (1H, s), 7.09 (2H, d, J=8.5 Hz), 7.23 (2H, d, J=8.5 Hz)

REFERENCE PRODUCTION EXAMPLE 3

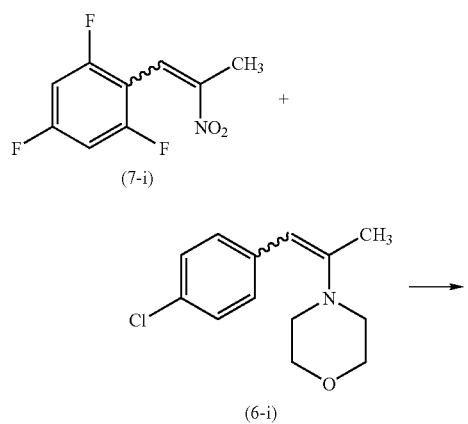

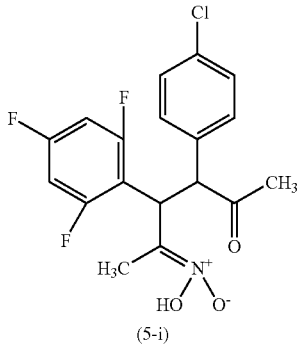

In 5 ml of toluene was dissolved 3.34 g of the compound represented by the formula (6-i), and the mixture was allowed to cool to 0° C. under nitrogen atmosphere. To the solution was added 3.05 g of the compound represented by the formula (7-i), and the mixture was stirred at the same temperature for 40 minutes and then at room temperature for overnight. After that, the reaction mixture was concentrated under reduced pressure. To the residue were added 15 ml of ethanol and 10 ml of 1 mol/L hydrochloric acid, and the mixture was stirred for overnight. The reaction mixture was concentrated under reduced pressure. The resulting solid residue was collected by filtration, and the solid was washed with a mixture of hexane and tert-butyl methyl ether. The resulting solid was dried under reduced pressure to obtain 1.82 g of the crude compound represented by the formula (5-i).

$^1$H-NMR (CDCl$_3$, TMS) δ (ppm): 1.52 (3H, s), 1.93 (3H, s), 3.32 (2H, d, J=11.7 Hz), 4.56 (2H, d, J=11.7 Hz), 6.60 (2H, br), 7.18-7.28 (4H, m)

REFERENCE PRODUCTION EXAMPLE 4

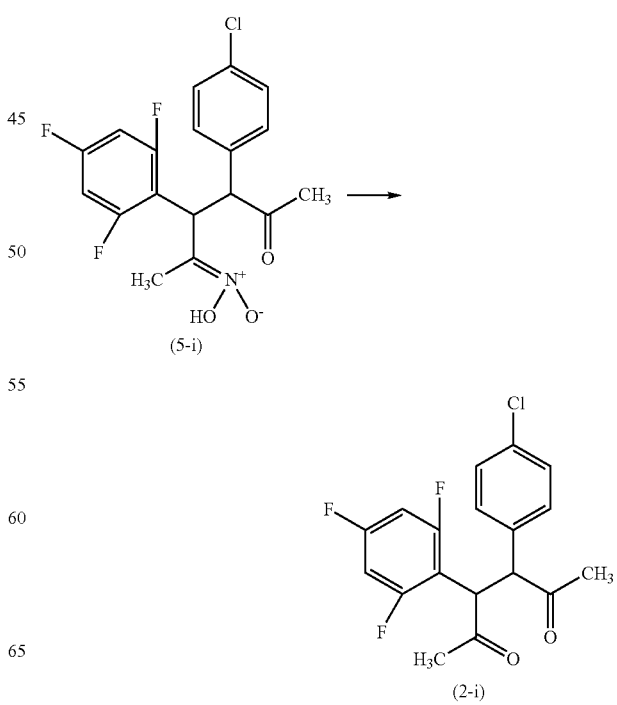

In 20 ml of a mixed solvent of ethanol:dioxane (1:1) was dissolved 1.82 g of the crude compound represented by the formula (5-i), to which 10 ml of 1 mol/L hydrochloric acid was added, and the mixture was stirred at room temperature for 6 hours. After that, the reaction mixture was concentrated under reduced pressure. The residue was subjected to silica gel column chromatography to obtain 0.76 g of the compound represented by the formula (2-i).

¹H-NMR (CDCl₃, TMS) δ (ppm): 2.06 (3H, s), 2.22 (3H, s), 4.52 (1H, d, J=11.0 Hz), 4.90 (1H, d, J=11.0 Hz), 6.52 (2H, t, J=8.5 Hz), 7.01 (2H, d, J=8.3 Hz), 7.13 (2H, d, J=8.3 Hz)

REFERENCE PRODUCTION EXAMPLE 5

A mixture of 7.41 g of the compound represented by the formula (A-ii), 14.37 g of morpholine dissolved in 30 ml of toluene, and 200 ml of toluene was cooled to 0° C. under nitrogen atmosphere. To the mixture was added dropwise a mixed solution of 30 ml of toluene and 28 ml of titanium tetrachloride (1.0 M toluene solution) over 1 hour, and the mixture was stirred at room temperature for overnight. The reaction mixture was filtered through Celite. The filtrate was concentrated under reduced pressure. To the residue was added hexane, and the generated solid was collected by filtration. The solid was washed with hexane twice, and dried under reduced pressure to obtain 5.38 g of the compound represented by the formula (6-ii).

¹H-NMR (CDCl₃, TMS) δ (ppm): 1.97 (3H, s), 2.32 (3H, s), 2.99 (4H, t, J=4.9 Hz), 3.79 (4H, t, J=4.9 Hz), 5.54 (1H, s), 7.08 (4H, m)

REFERENCE PRODUCTION EXAMPLE 6

In 6 ml of toluene was dissolved 5.38 g of the compound represented by the formula (6-ii), and the mixture was allowed to cool to 0° C. under nitrogen atmosphere. To the solution was added 4.30 g of the compound represented by the formula (7-i), and the mixture was stirred at the same temperature for 40 minutes and then at room temperature for 3 hours. After that, the reaction mixture was concentrated under reduced pressure. To the residue were added 12 ml of ethanol and 5 ml of 1 mol/L hydrochloric acid, and the mixture was stirred for 3 hours. The reaction mixture was concentrated under reduced pressure. The resulting solid residue was collected by filtration, and the solid was washed with a mixture of hexane and tert-butyl methyl ether. The resulting solid was dried under reduced pressure to give 4.93 g of the crude compound represented by the formula (5-ii)

¹H-NMR (CDCl₃, TMS) δ (ppm): 1.54 (3H, s), 1.92 (3H, s), 2.27 (3H, s), 3.28 (1H, d, J=11.0 Hz), 4.56 (1H, d, J=11.0 Hz), 6.54 (2H, br), 6.97 (2H, d J=8.0 Hz), 7.12 (2H, br)

REFERENCE PRODUCTION EXAMPLE 7

In 60 ml of a mixed solution of ethanol, methanol and dioxane (mixing ratio: ethanol/methanol/dioxane=1/1/1) was dissolved 4.93 g of the crude compound represented by the formula (5-ii), to which 20 ml of 1 mol/L hydrochloric acid was added, and the mixture was stirred at room temperature for 4 hours. The reaction mixture was concentrated under reduced pressure, and the residue was subjected to silica gel column chromatography to obtain 1.16 g of the compound represented by the formula (2-ii).

$^1$H-NMR (CDCl$_3$, TMS) δ (ppm): 2.07 (3H, s), 2.20 (3H, s), 2.22 (3H, s), 4.51 (1H, d, J=11.0 Hz), 4.92 (1H, d, J=11.0 Hz), 6.50 (2H, t, J=8.5 Hz), 6.94 (4H, s)

REFERENCE PRODUCTION EXAMPLE 8

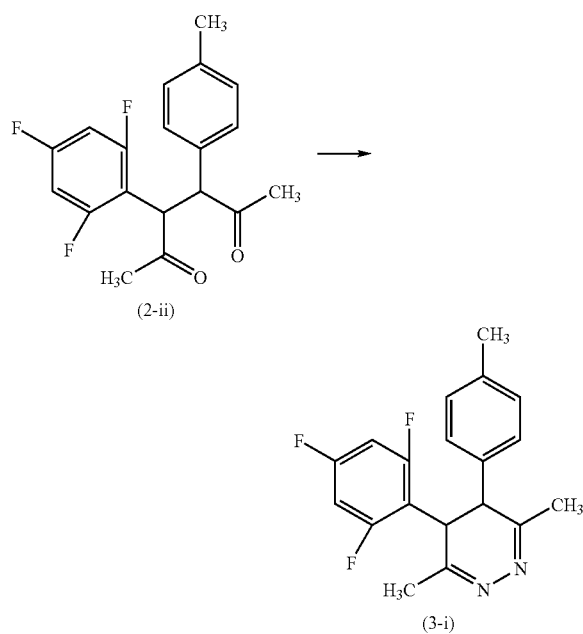

1.05 g of the compound represented by the formula (2-ii), 0.16 g of hydrazine monohydrate, and 12 ml of ethanol were mixed and the mixture was stirred at room temperature for 3 hours. The reaction mixture was concentrated under reduced pressure to obtain 1.09 g of the crude compound represented by the formula (3-i).

$^1$H-NMR (CDCl$_3$, TMS) δ (ppm): 1.95 (3H, s), 2.00 (3H, s), 2.29 (3H, s), 3.62 (1H, d, J=12.0 Hz), 3.93 (1H, d, J=12.0 Hz), 6.59 (2H, t, J=8.3 Hz), 6.96 (2H, d, J=8.0 Hz), 7.07 (2H, d, J=8.0 Hz)

REFERENCE PRODUCTION EXAMPLE 9

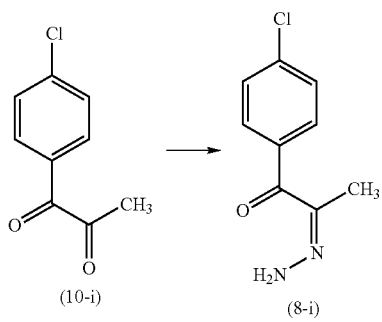

In 100 ml of ethanol was dissolved 21.90 g of the compound represented by the formula (10-i), to which was added dropwise a mixture of 6.00 g of hydrazine monohydrate and 20 ml of ethanol under nitrogen atmosphere while cooling it with ice. After the mixture was stirred at the same temperature for 1 hour and then at room temperature for 2 hours, it was allowed to stand at room temperature overnight. To the reaction mixture was added 80 ml of chloroform, and the mixture was filtered. The filtrate was concentrated under reduced pressure to obtain 23.52 g of the compound represented by the formula (8-i).

$^1$H-NMR (CDCl$_3$, TMS) δ (ppm): 2.05 (3H, s), 6.09 (2H, br s), 7.38 (2H, d, J=8 Hz), 7.81 (2H, d, J=8 Hz)

REFERENCE PRODUCTION EXAMPLE 10

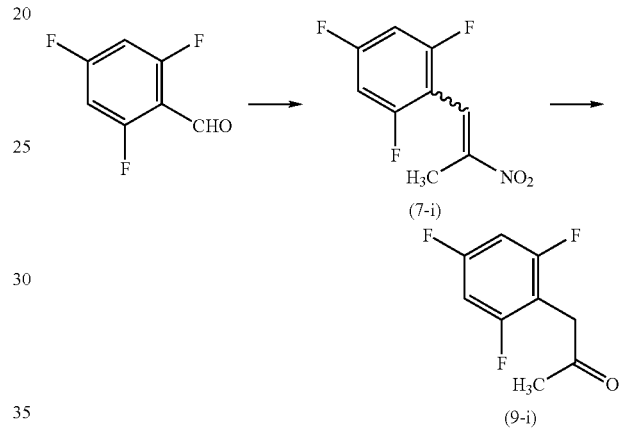

A mixture of 29.08 g of 2,4,6-trifluorobenzaldehyde, 4.34 g of ammonium acetate and 112 ml of nitroethane was heated to reflux under nitrogen atmosphere for 5 hours. The reaction mixture was allowed to cool to room temperature and concentrated under reduced pressure. To the residue was added chloroform, which was washed with saturated brine twice. After the organic layer was dried over anhydrous sodium sulfate, it was concentrated under reduced pressure to obtain 38.53 g of the crude compound represented by the formula (7-i).

To a mixture of 35.84 g of the crude compound represented by the formula (7-i), 35.58 g of 100-mesh iron powder, 1.09 g of ferric chloride (III) hexahydrate and 79 ml of water was added dropwise 64 ml of conc-hydrochloric acid in an oil bath having a temperature of 100° C. over 3 hours while stirring it. The mixture was stirred at the same temperature for 4 hours. The reaction mixture was allowed to cool to room temperature, to which were added water and chloroform, which was filtered through Celite. The filtrate was separated to two layers. The aqueous layer was extracted with chloroform. The organic layers were collected, which was washed with saturated brine twice, dried over anhydrous sodium sulfate, and concentrated under reduced pressure. The residue was subjected to silica gel column chromatography to obtain 15.09 g of the compound represented by the formula (9-i).

$^1$H-NMR (CDCl$_3$, TMS) δ (ppm)): 2.27 (3H, s), 3.74 (2H, s), 6.6-6.7 (2H, m)

REFERENCE PRODUCTION EXAMPLE 11

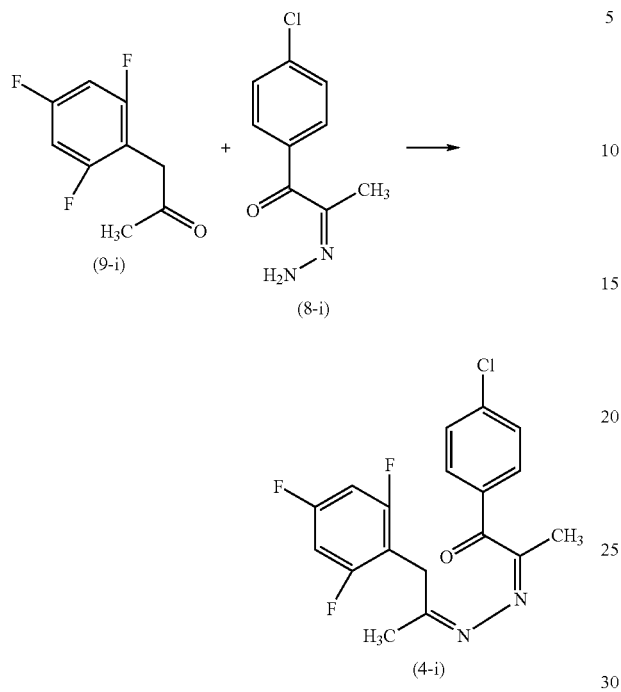

In 50 ml of toluene were dissolved 1.92 g of the compound represented by the formula (8-i) and 1.88 g of the compound represented by the formula (9-i), to which 60 mg of p-toluenesulfonic acid monohydrate, which was stirred at heat-reflux for 1 hour while dehydrating it with a Dean-Stark trap. The reaction mixture was allowed to cool to room temperature and was diluted with ethyl acetate, which was washed with saturated aqueous sodium bicarbonate solution. The organic layer was washed with saturated brine, dried, and concentrated under reduced pressure to obtain 3.52 g of the crude compound represented by the formula (4-i).

REFERENCE PRODUCTION EXAMPLE 12

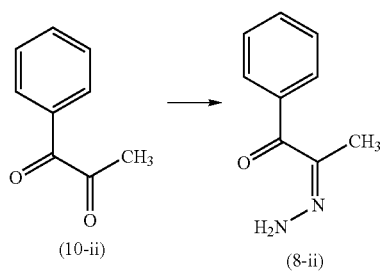

In 100 ml of ethanol was dissolved 29.63 g of the compound represented by the formula (10-ii), to which were added dropwise a mixture of 10.00 g of hydrazine monohydrate and 30 ml of ethanol under nitrogen atmosphere while ice-cooling. This mixed solution was stirred at the same temperature for 1.5 hours. The reaction mixture was filtered, and the filtrate was concentrated under reduced pressure to obtain 32.95 g of the compound represented by the formula (8-ii).

$^1$H-NMR (CDCl$_3$, TMS)$_\delta$(ppm): 2.03 (3H, s), 6.09 (2H, br s), 7.35-7.50 (3H, m), 7.80-7.85 (2H, m)

REFERENCE PRODUCTION EXAMPLE 13

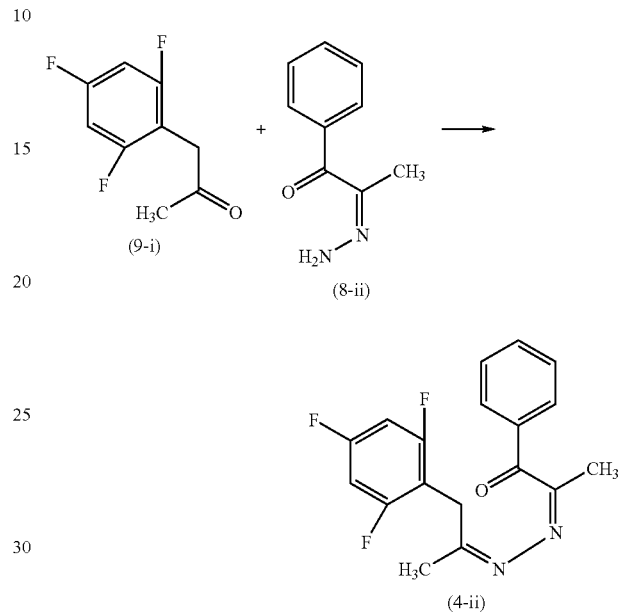

In 50 ml toluene were dissolved 1.78 g of the compound represented by the formula (8-ii) and 1.88 g of the compound represented by the formula (9-i), to which 60 mg of p-toluenesulfonic acid monohydrate was added, and the mixture was stirred at heat-reflux for 1 hour while it was dehydrated with a Dean-Stark trap. The reaction mixture was allowed to cool to room temperature and diluted with ethyl acetate, which was washed with saturated aqueous sodium bicarbonate solution. The organic layer was washed with saturated brine, dried, and concentrated under reduced pressure. The residue was subjected to silica gel column chromatography to obtain 2.75 g of the crude compound represented by the formula (4-ii).

REFERENCE PRODUCTION EXAMPLE 14

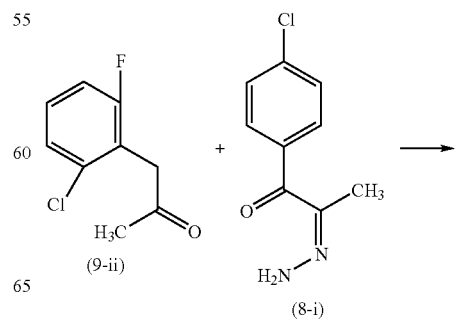

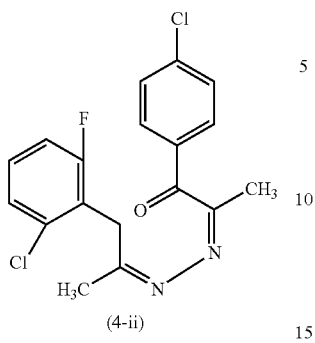

(4-ii)

In 20 ml of toluene were dissolved 0.68 g of the compound represented by the formula (8-i) and 0.65 g of the compound represented by the formula (9-ii), to which 20 mg of p-toluenesulfonic acid monohydrate was added, and the mixture was stirred at heat-reflux for 1 hour while it was dehydrated with a Dean-Stark trap. The reaction mixture was allowed to cool to room temperature and diluted with ethyl acetate, which was washed with saturated aqueous sodium bicarbonate solution. The organic layer was washed with saturated brine, dried and concentrated under reduced pressure to obtain 1.34 g of the compound represented by the formula (4-iii).

REFERENCE PRODUCTION EXAMPLE 15

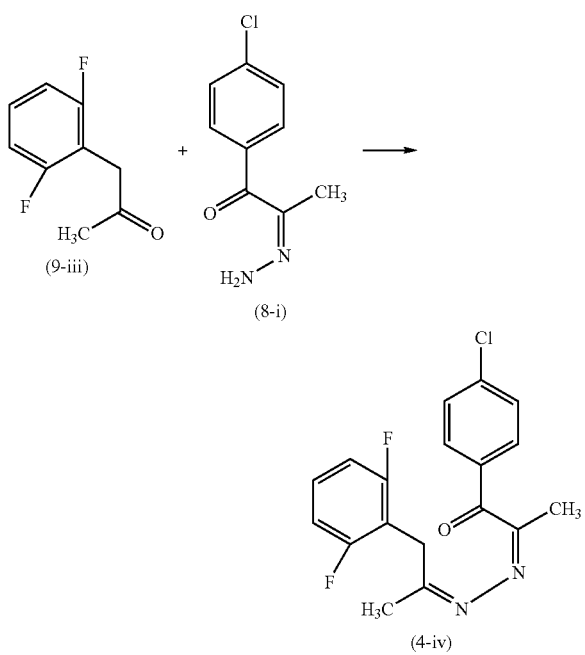

In 50 ml of toluene were dissolved 1.97 g of the compound represented by the formula (8-i) and 1.70 g of the compound represented by the formula (9-iii), to which 10 mg of p-toluenesulfonic acid monohydrate was added, and the mixture was stirred at heat-reflux for 1.5 hours while it was dehydrated with a Dean-Stark trap. The reaction mixture was allowed to cool to room temperature and concentrated under reduced pressure to obtain 3.44 g of the crude compound represented by the formula (4-iv).

REFERENCE PRODUCTION EXAMPLE 16

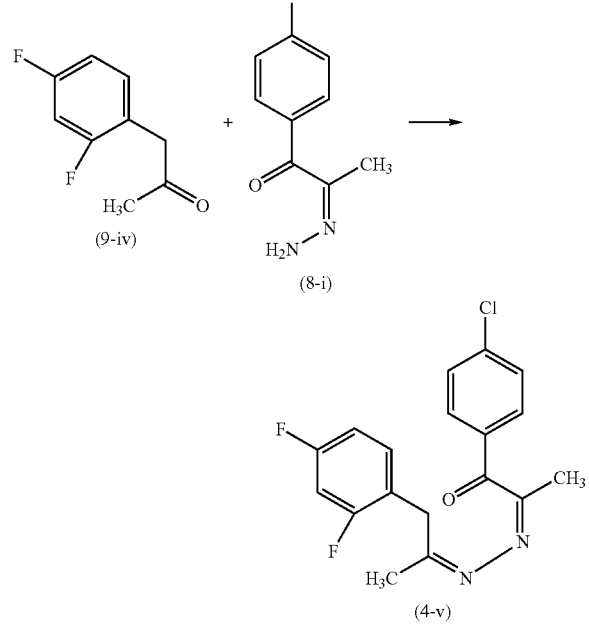

In 50 ml of toluene were dissolved 1.97 g of the compound (8-i) and 1.70 g of the compound represented by the formula (9-iv), to which 10 mg of p-toluenesulfonic acid monohydrate was added, and the mixture was stirred at heat-reflux for 1.5 hour while it was dehydrated with a Dean-Stark trap. The reaction mixture was allowed to cool to room temperature and concentrated under reduced pressure to obtain 3.64 g of the crude compound represented by the formula (4-v).

REFERENCE PRODUCTION EXAMPLE 17

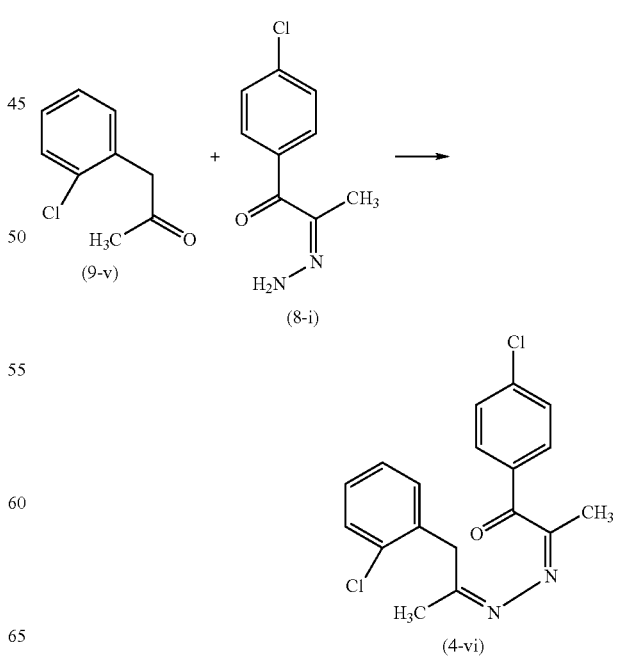

In 25 ml of toluene were dissolved 1.97 g of the compound represented by the formula (8-i) and 1.69 g of the compound represented by the formula (9-v), to which 10 mg of p-toluenesulfonic acid monohydrate, and the mixture was stirred at heat-reflux for 1.5 hours while it was dehydrated with a Dean-Stark trap. The reaction mixture was allowed to cool to room temperature and concentrated under reduced pressure to obtain 3.71 g of the crude compound represented by the formula (4-vi).

REFERENCE PRODUCTION EXAMPLE 18

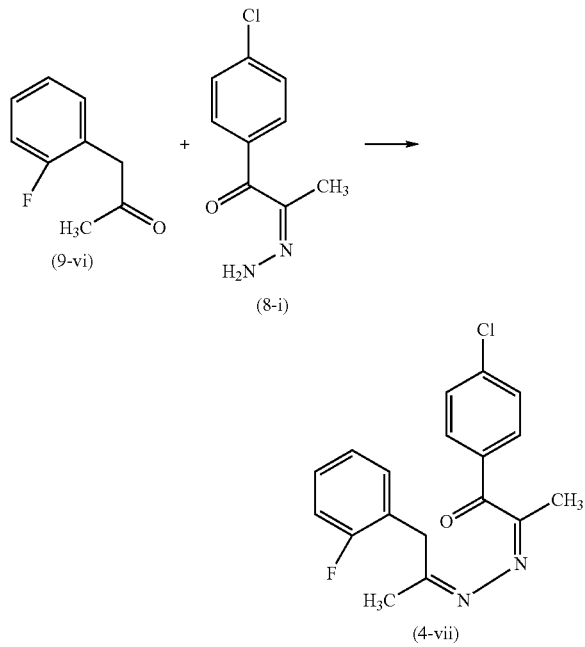

In 30 ml of toluene were dissolved 1.97 g of the compound represented by the formula (8-i) and 1.52 g of the compound represented by the formula (9-vi), to which 10 mg of p-toluenesulfonic acid monohydrate, and the mixture was stirred at heat-reflux 1.5 hours while it was dehydrated with a Dean-Stark trap. The reaction mixture was allowed to cool to room temperature and concentrated under reduced pressure to obtain 3.30 g of the compound represented by the formula (4-vii).

REFERENCE PRODUCTION EXAMPLE 19

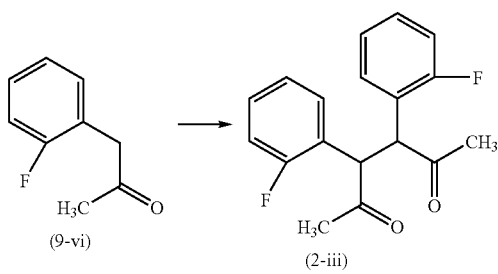

In 20 ml of acetic acid was dissolved 4.99 g of the compound represented by the formula (9-vi), to which 1.70 g of activated manganese dioxide, and the mixture was heated to reflux under nitrogen atmosphere for 7 hours. The reaction mixture was allowed to cool to room temperature and poured into a mixture of brine and ice, which was extracted with toluene. The organic layer was washed with saturated brine, dried, and concentrated under reduced pressure. The residue was subjected to silica gel column chromatography (eluent: hexane-ethyl acetate) to obtain 0.84 g of the compound represented by the formula (2-iii).

$^1$H-NMR (CDCl$_3$, TMS) δ (ppm): 2.16 (6H, s), 4.92 (2H, s), 6.8-7.2 (8H)

Next, Formulation examples are shown. Part means part by weight.

FORMULATION EXAMPLE 1

Fifty parts of each of compounds (i) to (x) of the present invention, 3 parts of calcium lignin sulfonate, 2 parts of magnesium laurylsulfate and 45 parts of synthetic hydrated silica are pulverized and mixed well to give wettable powders of each compound.

FORMULATION EXAMPLE 2

Twenty parts of each of compounds (i) to (x) of the present invention and 1.5 parts of sorbitan trioleate are mixed with 28.5 parts of an aqueous solution containing 2 parts of polyvinyl alcohol, and wet-pulverized finely. To the obtained mixture, 40 parts of an aqueous solution containing 0.05 part of xanthan gum and 0.1 part of aluminum magnesium silicate is added and further 10 parts of propylene glycol are added to give a flowable of each compound.

FORMULATION EXAMPLE 3

Two parts of each of compounds (i) to (x) of the present invention, 88 parts of kaolin clay and 10 parts of talc are pulverized and mixed well to give a dust of each compound.

FORMULATION EXAMPLE 4

Five parts of each of compounds (i) to (x) of the present invention, 14 parts of polyoxyethylenestyryl phenyl ether, 6 parts of calcium dodecylbenzenesulfonate and 75 parts of xylene are mixed well to give an emulsifiable concentrate of each compound.

FORMULATION EXAMPLE 5

Two parts of each of compounds (i) to (x) of the present invention, 1 part of synthetic hydrated silica, 2 parts of calcium ligninsulfonate, 30 parts of bentonite and 65 parts of kaolin clay are pulverized and mixed well, and water is added thereto and kneaded, granulated and dried to give a granule of each compound.

FORMULATION EXAMPLE 6

Ten parts of each of the compounds (i) to (x) of present invention, 35 parts of white carbon containing 50 parts of ammonium polyoxyethylenealkyl ether sulfate and 55 parts of water are mixed and wet pulverized finely to give a formulation of each compound.

Next, a fact that the compound of the present invention is effective for controlling plant diseases is shown by test examples.

TEST EXAMPLE 1

A plastic pot was filled with sandy loam, cucumber (cultivar: Sagami Hanjiro) was sowed, and grown in a greenhouse for 10 days. Each of the compounds (i) to (x) of the present invention was formulated according to Formulation Example 6, then, diluted with water to a concentration of 500 ppm. Each of the resulting diluted solutions was sprayed on stem and leaves so as to sufficiently adhere to the surface of cucumber cotyledones. After spraying, the plant was air-dried, and a PDA medium containing spores of *Botrytis cinerea* was placed on the surface of cucumber cotyledons. Then, the cucumber was left under humid condition at 12° C. for 5 days. Thereafter, the lesion area of the plant was visually observed. As a result, the lesion area of the cucumber treated with the compounds (i) to (x) of the present invention was 10% or less of the lesion area of non-treated cucumber.

TEST EXAMPLE 2

A plastic pot was filled with sandy loam, paddy (cultivar: NihonBare) was sowed, and grown in a greenhouse for 15 days. Each of the compounds (i) to (x) of the present invention was formulated according to Formulation Example 6, then, diluted with water to a concentration of 500 ppm. Each of the resulting diluted solutions was sprayed on stem and leaves so as to sufficiently adhere to the surface of the paddy leaves. After spraying, the plant was air-dried. Plastic pots containing planted paddy affected by *Pyricularia oryzae* were placed around the plastic pot of paddy, and this condition was left under humid condition at 22° C. for 6 days. Thereafter, a controlling effect was checked. As a result, the lesion area of the paddy treated with the compounds (i) to (x) of the present invention was 10% or less of the lesion area of non-treated paddy.

TEST EXAMPLE 3

A plastic pot was filled with sandy loam, Japanese radish (cultivar: Wase 40 nichi) was sowed, and grown in a greenhouse for 5 days. Each of the compounds (i) to (x) of the present invention was formulated according to Formulation Example 6, then, diluted with water to a concentration of 500 ppm. Each of the resulting diluted solutions was sprayed on stem and leaves so as to sufficiently adhere to the radish. After spraying, the plant was air-dried, and inoculated with spores of *Alternaria brassicicola*. Then, this radish was left under humid condition at 23° C. overnight, further, left in a greenhouse for 3 days. Thereafter, a controlling effect was checked. As a result, the lesion area of the radish treated with the compounds (i) to (x) of the present invention was 10% or less of the lesion area of non-treated radish.

INDUSTRIAL APPLICABILITY

The plant diseases can be controlled by using the compound of the present invention.

The invention claimed is:
1. A pyridazine compound represented by formula (1):

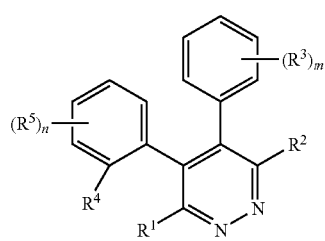

(1)

wherein,
$R^1$ and $R^2$ are same or different and represent a C1-C4 alkyl group;
$R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;
m represents an integer of 0 to 5; provided that, when m represents an integer of 2 or more, each of $R^3$s is same or different;
$R^4$ represents a halogen atom, a nitro group, a cyano group, a C1-C4 alkyl group optionally substituted by at least one halogen atom or a C1-C4 alkoxy group optionally substituted by at least one halogen atom;
$R^5$ represents a halogen atom, a nitro group, a cyano group, a C1-C4 alkyl group optionally substituted by at least one halogen atom or a C1-C4 alkoxy group optionally substituted by at least one halogen atom;
n represents an integer of 0 to 4; provided that, when n represents an integer of 2 or more, each of $R^5$s is same or different.

2. The pyridazine compound according to claim 1, wherein n is 0, 1 or 2 and m is 1 or 2 in the formula (1).

3. The pyridazine compound according to claim 1, wherein each of $R^1$ and $R^2$ is a methyl group, and $R^4$ is a halogen atom in the formula (1).

4. A fungicidal composition comprising the pyridazine compound according to claim 1 as an active ingredient.

5. A compound represented by formula (3):

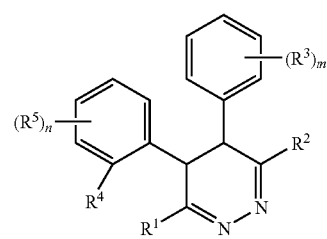

(3)

wherein,
$R^1$ and $R^2$ are same or different and represent a C1-C4 alkyl group;
$R^3$ represents a halogen atom, a nitro group, a cyano group, a C1-C4 alkyl group optionally substituted by at least one halogen atom, a C1-C4 alkoxy group optionally substituted by at least one halogen atom or a C1-C4 alkylthio group optionally substituted by at least one halogen atom;
m represents an integer of 0 to 5; provided that, when m represents an integer of 2 or more, each of $R^3$s is same or different;
$R^4$ represents a halogen atom, a nitro group, a cyano group, a C1-C4 alkyl group optionally substituted by at least one halogen atom or a C1-C4 alkoxy group optionally substituted by at least one halogen atom;
$R^5$ represents a halogen atom, a nitro group, a cyano group, a C1-C4 alkyl group optionally substituted by at least one halogen atom or a C1-C4 alkoxy group optionally substituted by at least one halogen atom;
n represents an integer of 0 to 4; provided that, when n represents an integer of 2 or more, each of $R^5$s is same or different.

* * * * *